(12) United States Patent
Chatterjee et al.

(10) Patent No.: US 11,306,224 B2
(45) Date of Patent: *Apr. 19, 2022

(54) ARTICLES COMPRISING (METH)ACRYLATE PRESSURE-SENSITIVE ADHESIVE WITH ENHANCED ADHESION TO WET SURFACES

(71) Applicant: 3M INNOVATIVE PROPERTIES COMPANY, St. Paul, MN (US)

(72) Inventors: Joon Chatterjee, Gaithersburg, MD (US); Vinod P. Menon, Woodbury, MN (US); Roberta K. Sadi, São Paulo (BR)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 576 days.

This patent is subject to a terminal disclaimer.

(21) Appl. No.: 15/754,231

(22) PCT Filed: Aug. 19, 2016

(86) PCT No.: PCT/US2016/047824
§ 371 (c)(1),
(2) Date: Feb. 21, 2018

(87) PCT Pub. No.: WO2017/040072
PCT Pub. Date: Mar. 9, 2017

(65) Prior Publication Data
US 2018/0298240 A1      Oct. 18, 2018

Related U.S. Application Data

(60) Provisional application No. 62/212,131, filed on Aug. 31, 2015.

(51) Int. Cl.
*C09J 7/38* (2018.01)
*C09J 133/08* (2006.01)
(Continued)

(52) U.S. Cl.
CPC ............ *C09J 7/385* (2018.01); *A61B 5/6832* (2013.01); *A61B 18/16* (2013.01); *A61F 5/443* (2013.01);
(Continued)

(58) Field of Classification Search
None
See application file for complete search history.

(56) References Cited

U.S. PATENT DOCUMENTS 2,884,126 A    4/1959  Ulrich
4,379,881 A    4/1983  Peck
(Continued)

FOREIGN PATENT DOCUMENTS

CN    1136814      11/1996
CN    102850982    1/2013
(Continued)

OTHER PUBLICATIONS

Aldrich Data Sheet (Year: 2019).*
(Continued)

*Primary Examiner* — Frank D Ducheneaux
(74) *Attorney, Agent, or Firm* — 3M Innovative Properties Company

(57) ABSTRACT

Articles comprising pressure-sensitive adhesives with enhanced adhesion to wet surfaces, obtained from crosslinking a pre-adhesive composition comprising poly(meth)acrylate macromolecules that comprise a number-average molecular weight of from about 25000 to about 200000, and methods of using such articles.

20 Claims, 4 Drawing Sheets

(51) Int. Cl.
*A61B 18/16* (2006.01)
*A61F 5/443* (2006.01)
*C08F 20/14* (2006.01)
*C08J 3/28* (2006.01)
*C09J 11/06* (2006.01)
*A61B 5/00* (2006.01)
*A61N 1/04* (2006.01)

(52) U.S. Cl.
CPC ......... *A61N 1/0456* (2013.01); *A61N 1/0496* (2013.01); *C08F 20/14* (2013.01); *C08J 3/28* (2013.01); *C09J 11/06* (2013.01); *C09J 133/08* (2013.01); *C08F 2810/20* (2013.01); *C08J 2333/10* (2013.01); *C09J 2301/312* (2020.08); *C09J 2433/00* (2013.01)

(56) References Cited

U.S. PATENT DOCUMENTS

| | | |
|---|---|---|
| 5,543,151 A | 8/1996 | Shirai |
| 5,637,646 A | 6/1997 | Ellis |
| 5,753,768 A | 5/1998 | Ellis |
| 5,804,610 A | 9/1998 | Hamer |
| 5,814,685 A * | 9/1998 | Satake ............... C09D 11/326 523/201 |
| 5,986,011 A | 11/1999 | Ellis |
| 6,083,856 A | 7/2000 | Joseph |
| 6,121,508 A | 9/2000 | Bischof |
| 6,171,985 B1 | 1/2001 | Joseph |
| 6,198,016 B1 | 3/2001 | Lucast |
| 6,441,092 B1 | 8/2002 | Gieselman |
| 6,518,343 B1 | 2/2003 | Lucast |
| 6,624,273 B1 | 9/2003 | Everaerts |
| 6,855,386 B1 | 2/2005 | Daniels |
| 7,070,051 B2 * | 7/2006 | Kanner ............ A61B 17/06133 206/382 |
| 7,520,872 B2 | 4/2009 | Biggie |
| 7,691,437 B2 | 4/2010 | Ellis |
| 7,968,661 B2 | 6/2011 | Ellis |
| 8,137,807 B2 | 3/2012 | Clapper |
| 8,337,961 B2 | 12/2012 | Kim |
| 8,389,001 B2 | 3/2013 | Kamiyama |
| 8,541,481 B2 | 9/2013 | Determan |
| 2001/0029956 A1 | 10/2001 | Argenta |
| 2003/0008140 A1 | 1/2003 | Takizawa |
| 2003/0050613 A1 | 3/2003 | Hammerslag |
| 2003/0171454 A1 | 9/2003 | Lucast |
| 2003/0216519 A1 * | 11/2003 | Heilmann ............ C09D 201/08 525/191 |
| 2005/0181148 A1 | 8/2005 | Kim |
| 2005/0202070 A1 | 9/2005 | Wang |
| 2007/0142499 A1 | 6/2007 | Wang |
| 2011/0009838 A1 | 1/2011 | Greener |
| 2011/0066123 A1 | 3/2011 | Tout |
| 2012/0302041 A1 | 11/2012 | Maeda |
| 2013/0131616 A1 | 5/2013 | Locke |
| 2014/0316359 A1 | 10/2014 | Collinson |
| 2015/0044457 A1 | 2/2015 | Chen |

FOREIGN PATENT DOCUMENTS

| | | |
|---|---|---|
| CN | 102222633 | 7/2014 |
| DE | 102012218335 | 4/2013 |
| EP | 0902816 | 3/1999 |
| WO | WO 1995-09876 | 4/1995 |
| WO | WO 00/78884 | 12/2000 |
| WO | WO 2007-124017 | 11/2007 |
| WO | WO 2008-063281 | 5/2008 |
| WO | WO 2010-129299 | 11/2010 |
| WO | WO 2011-153308 | 12/2011 |
| WO | WO 2012-069794 | 5/2012 |
| WO | WO 2012-148608 | 11/2012 |
| WO | WO 2013-048735 | 4/2013 |
| WO | WO 2013-066401 | 5/2013 |
| WO | WO 2014-078123 | 5/2014 |
| WO | WO 2015-134249 | 9/2015 |
| WO | WO 2017-040074 | 3/2017 |

OTHER PUBLICATIONS

Callewaer, "Artificial Sweat Composition to Grow and Sustain a Mixed Human Axillary Microbiome", Journal of Microbiological Methods, 2014, vol. 103, pp. 6-8.

Czech, "2-Ethylhexyl acrylate/4-acryloyloxy benzophenone copolymers as UV-crosslikable pressure-sensitive adhesives", Polymer Bulletin 52, 2004, pp. 283-288.

Czech, "Photoreactive UV-Crosslinkable Pressure-Sensitive Adhesives Based on Butyl Acrylate and 4-Acryloyloxy Benzophenone Copolymers", Journal of Research Updates in Polymer Science, 2012, vol. 1, No. 2, pp. 96-100.

Czech, "Pressure-Sensitive Adhesives for Medical Applications", Wide Spectra of Quality Control, 309-332 (2011).

Davies, "A quantitative kinetic theory of emulsion type, I. Physical chemistry of the emulsifying agent, Gas/Liquid and Liquid/Liquid Interface", Proceedings of the International Congress of Surface Activity, 1957, pp. 426-438.

Gerhardt, "Fabrication, Characterisation and Tribological Investigation of Artificial Skin Surface Lipid Films", Tribology Letters, 2009, vol. 34, pp. 81-93.

Lester; Acrylic Pressure Sensitive Adhesives Having Controlled Placement of Functional Groups, Pressure Sensitive Tape Council; 2009, pp. 147-155.

Rodriguez, "Principles of Polymer Systems", 221 (1982).

Sheu, "Human Skin Surface Lipid Film: an Ultrastructural Study and Interaction with Corneocytes and Intercellular Lipid Lamellae of the Stratum Corneum", British Journal of Dermatology, 1999, vol. 140, pp. 385-391.

Extended European Search Report, EP15758972.2, PCT/US2015/017489, dated Sep. 22, 2017, 3 pgs.

International Search Report for PCT International Application No. PCT/US2016/47884, dated Nov. 18, 2016, 2pgs.

Search Report for CN201680048843.6 dated Aug. 31, 2018, 2 pgs.

Supplementary European Search Report for EP 16842586 dated Mar. 19, 2019.

* cited by examiner

US 11,306,224 B2

ARTICLES COMPRISING (METH)ACRYLATE PRESSURE-SENSITIVE ADHESIVE WITH ENHANCED ADHESION TO WET SURFACES

CROSS REFERENCE TO RELATED APPLICATIONS

This application is a national stage filing under 35 U.S.C. 371 of PCT/US2016/047824, filed Aug. 19, 2016, which claims the benefit of U.S. Provisional Application No. 62/212,131, filed Aug. 31, 2015, the disclosures of which are incorporated by reference in their entirety herein.

BACKGROUND (Meth)acrylate pressure-sensitive adhesives (PSAs) are attractive materials for many applications. (Meth)acrylates are known for their optical clarity, oxidative resistance, and inherently tacky nature. However, many such (meth)acrylate polymers are hydrophobic in nature and, without modification, have been generally considered to be unsuitable as "wet-stick" adhesives (e.g., pressure-sensitive adhesives that are capable of adhering satisfactorily to wet or moist surfaces, particularly skin); see e.g. U.S. Pat. Nos. 6,518,343 and 6,441,092.

SUMMARY

In broad summary, herein are disclosed pressure-sensitive adhesives obtained from crosslinking a pre-adhesive composition comprising poly(meth)acrylate macromolecules that comprise a number-average molecular weight of from about 25000 to about 200000. Also disclosed are articles comprising such an adhesives, and methods of using such articles. In at least some embodiments, such adhesives exhibit wet-stick properties as disclosed herein. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

DETAILED DESCRIPTION

Definitions

Figure 1:
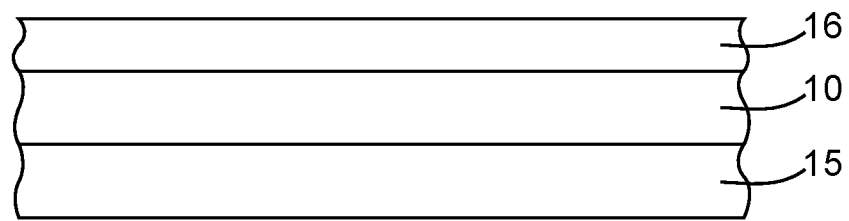
FIG. 1 is an idealized side view of an exemplary article comprising a pressure-sensitive adhesive as disclosed herein.

As used herein, the term "pressure-sensitive adhesive" refers to a viscoelastic material that meets the well-known Dahlquist criterion (e.g., the storage modulus of the material at 25° C. is less than $3\times10^5$ Pa at a frequency of 1 Hz).

As used herein, the term "pre-adhesive composition" refers to a collection of poly(meth)acrylate macromolecules of number-average molecular weight of about 25000 to 200000, optionally along with one or more ingredients such as e.g. plasticizers, tackifiers, solvents, stabilizers, processing aids, and so on. While a pre-adhesive composition may not necessarily exhibit pressure-sensitive properties, it can be crosslinked to provide a pressure-sensitive adhesive as disclosed herein.

As used herein, the term "(meth)acrylate" refers to an acrylate, methacrylate, or both. The term "(meth)acrylate" refers a monomer of formula $CH_2=C(R^1)-(CO)-OR^2$ where $R^2$ is an alkyl, heteroalkyl, alkenyl, or aryl (or, a monomer unit derived from such a monomer). An alkyl, heteroalkyl, or alkenyl $R^2$ group can be substituted with an aryl, aryloxy, halo, or a combination thereof. An aryl $R^2$ group can be substituted with an alkyl, heteroalkyl, halo, alkoxy, aryloxy, or a combination thereof. The term "alkyl (meth)acrylate" refers to a (meth)acrylate where $R^2$ is an alkyl group.

As used herein, the term "wet-stick" pressure-sensitive adhesive refers to a pressure-sensitive adhesive that exhibits a Peak Pull Force of at least about 2000 g when tested in the Wet-Stick Test Method disclosed herein.

As used herein, the term "annular" is used in a general sense to signify an item that surrounds a central region and does not require that the item exhibit a shape that is substantially, or even generally, circular. (For example, an "annular" PSA of an electrode may take the form of e.g. a rectangular picture-frame border.)

As will be appreciated by those of ordinary skill, terminology such as "consisting essentially of" a certain component, or such as being "substantially free of" of a particular material, does not preclude the presence of some extremely low, (i.e., 0.05 wt. % or less), amount of such material, as may occur e.g. when using large scale production equipment subject to customary cleaning procedures.

All parts and percentages disclosed herein are on a weight basis, unless otherwise indicated. All molecular weights (e.g., $M_n$) are in grams per mole.

Pressure-Sensitive Adhesive/Pre-Adhesive Composition

Pressure-sensitive adhesives (PSAs) and articles comprising such adhesives are disclosed herein. The pressure-sensitive adhesives contain a networked (meth)acrylate material prepared by crosslinking a pre-adhesive composition comprising poly(meth)acrylate macromolecules that comprise a number-average molecular weight of from about 25000 to about 200000. As will be appreciated from the disclosures herein, such pre-adhesive compositions can exhibit a unique rheology that provides the resulting PSAs with e.g. an enhanced ability to be removed from human skin with minimum perceived discomfort.

By "prepared by crosslinking a pre-adhesive composition", by "the crosslinking reaction product of a pre-adhesive composition", and similar terminology, is meant that a pre-adhesive composition (prepared e.g. from a first (meth) acrylate monomer mixture, in a first, synthesis reaction as described in detail later herein) is subjected to a crosslinking reaction in which at least some poly(meth)acrylate macromolecules of the pre-adhesive composition become covalently bonded to other macromolecules of the composition to form a polymer network that exhibits pressure-sensitive adhesive properties (noting that ingredients such as plasticizers and so on may be included to enhance the pressure-sensitive adhesive properties). Such a two-step process (i.e., the preparing of a pre-adhesive composition, and the subsequent crosslinking of such a composition), and the resulting pressure-sensitive adhesive product of such a process, can be distinguished from e.g. a polymer network that is built up from monomers/oligomers e.g. in a single synthesis process, as will be appreciated from the discussions herein.

By definition, the poly(meth)acrylate macromolecules of the pre-adhesive composition comprise a number average molecular weight (as may be determined e.g. by gel permeation chromatography using polystyrene standards as described in the Examples herein) of from about 25000 to about 200000 (grams per mole). As disclosed herein, it has been found that a molecular weight that is too low (e.g., below about 25000) may result in difficulty in crosslinking the pre-adhesive composition to form a suitable pressure-sensitive adhesive. Conversely, a molecular weight that is too high (e.g., above about 200000) may cause the crosslinked pressure-sensitive adhesive produced therefrom to exhibit a modulus that is too high (such that the PSA may e.g. lack optimum properties of tack and/or quick stick). In various embodiments, the poly(meth)acrylate macromolecules of the pre-adhesive composition may comprise a number average molecular weight of at least about 26000, 27000, 28000, 30000, or 32000. In further embodiments, the poly(meth)acrylate macromolecules of the pre-adhesive composition may comprise a number average molecular weight of at most about 110000, 100000, 80000, 60000, 40000, or 35000. All such molecular weights are below those of (meth)acrylate polymeric materials used in many conventional pressure-sensitive adhesives, with advantageous consequences as discussed herein. In some embodiments, the poly(meth)acrylate macromolecules may be essentially linear polymers (e.g., excepting such branching as may occasionally statistically occur in a polymerization reaction of (meth)acrylate monomers, e.g. monofunctional monomers.)

As documented in the Examples herein, the molecular weight of the macromolecules of a pre-adhesive composition (as well as the presence and/or amount of any plasticizer in the pre-adhesive composition) can have a significant impact on the modulus of the pre-adhesive composition, which can in turn have a significant effect on the properties of a PSA made therefrom. The pre-adhesive compositions disclosed herein have been found to exhibit a storage modulus in a range that helps provide advantageous properties (e.g., gentle release from skin) of the pressure-sensitive adhesives formed therefrom. By definition, the pre-adhesive composition exhibits a storage modulus of at most about 10000 Pa (as measured at 25° C., using procedures outlined in the Examples herein). In various embodiments the pre-adhesive composition may exhibit a storage modulus of at most about 7000, 4000 2000, 1000 or 500 Pa. In further embodiments the pre-adhesive composition may exhibit a storage modulus of at least about 4, 10, 20, 40, 80, 100, 200, or 400 Pa.

The pre-adhesive compositions as disclosed herein have been found to exhibit a glass transition temperature ($T_g$) that helps provide advantageous properties (e.g., gentle release from skin) of the pressure-sensitive adhesives formed therefrom. (For example, a lower $T_g$ is often associated with a lower value of peel adhesion.) By definition, the pre-adhesive composition exhibits a $T_g$ of at most about minus 20° C. (measured using procedures outlined in the Examples herein). In various embodiments the pre-adhesive composition may exhibit a $T_g$ of at most about minus 30° C., minus 35° C., minus 40° C., or minus 45° C. In further embodiments the pre-adhesive composition may exhibit a $T_g$ of at least about minus 60° C., minus 55° C., or minus 50° C.

As demonstrated in the Examples herein, it has been found that the molecular weight of the poly(meth)acrylate macromolecules of the pre-adhesive composition can affect the $T_g$ of the pre-adhesive composition. This can allow the $T_g$ of the pre-adhesive composition to be tailored for optimum properties of the pressure-sensitive adhesive made therefrom. The ordinary artisan will appreciate that the molecular weights of the poly(meth)acrylate macromolecules disclosed herein are sufficiently high that it would be expected that properties such as $T_g$ would have plateaued and thus would exhibit little change with molecular weight. For example, the poly(meth)acrylate macromolecules of Samples PRE-1, PRE-2, PRE-3, and PRE-4, comprise molecular weights that respectively correspond to a degree of polymerization (i.e., the average number of monomer units per macromolecular chain) in the range of about 130, 151, 187, and 300 (as noted in Table 3 of the Examples). These are all well over the threshold number of macromolecular chain atoms above which $T_g$ is expected to be relatively insensitive to changes in molecular weight (see e.g. Rodriguez, Principles of Polymer Systems ($2^{nd}$ Edition, 1982); Section 8-7, page 221). However, these samples respectively exhibited $T_g$s of minus 48° C., minus 42° C., minus 39° C., and minus 36° C. (as noted in Table 3 and FIG. 2). For comparison, the ordinary artisan would expect that the $T_g$ of conventional poly(isooctyl acrylate), e.g. at a molecular weight of e.g. >200000-500000, would be in the range of minus 30° C. to minus 35° C., when measured by the same method. (The artisan would also expect such a material to exhibit a modulus that is significantly higher than the moduli exhibited by the materials described herein.) The discovery that the molecular weight of the poly(meth)acrylate macromolecules of the pre-adhesive composition can be used as a result-effective variable to affect the $T_g$ of the pre-adhesive composition over the claimed range of molecular weight (and thus to affect the properties of the PSA made therefrom) is an unexpected result.

In some cases properties such as e.g. storage modulus and/or $T_g$ may be primarily, or essentially completely, derived from the properties of the poly(meth)acrylate macromolecules of the pre-adhesive composition (e.g., in the event that the pre-adhesive composition consists essentially of the poly(meth)acrylate macromolecules). However, in some embodiments one or more plasticizers may be included in the pre-adhesive composition. In such embodiments, properties such as the storage modulus, $T_g$, and/or the viscosity of the pre-adhesive composition may be slightly, or significantly, affected by the plasticizer. Thus, the amount and/or type of such a plasticizer may be conveniently chosen (e.g., in addition to the molecular weight of the poly(meth)acrylate macromolecules), to affect the properties of the pre-adhesive composition and of the PSA made therefrom, as documented in the Examples herein.

In embodiments in which one or more plasticizers are present in the pre-adhesive composition, they may be present at a wt. % (based on the total weight of the pre-adhesive composition) of at least about 2, 4, 8, 12, or 20. In further embodiments, such plasticizers may be present at a wt. % of at most about 50, 30, 20, 10, 4, 2, or 1. Any suitable plasticizer may be used as long as it does not unacceptably affect the properties of the pre-adhesive composition of the PSA made therefrom. Such a plasticizer may be optimally selected to be compatible with (i.e., miscible with) the other components in the pre-adhesive composition (e.g., the poly(meth)acrylate macromolecules). Potentially suitable plasticizers include various esters, e.g. adipic acid esters, formic acid esters, phosphoric acid esters, benzoic acid esters, phthalic acid esters; sulfonamides, and naphthenic oils. Other potentially suitable plasticizers include e.g. hydrocarbon oils (e.g., those that are aromatic, paraffinic, or naphthenic), vegetable oils, hydrocarbon resins, polyterpenes, rosin esters, phthalates, phosphate esters, dibasic acid esters, fatty acid esters, polyethers, and combinations thereof; plant fats and oils such as olive oil, castor oil, and palm oil; animal fats and oils such as lanolin; fatty acid esters of polyhydric alcohols such as a glycerin fatty acid ester and a propylene glycol fatty acid ester; and, fatty acid alkyl esters such as ethyl oleate, isopropyl palmitate, octyl palmitate, isopropyl myristate, isotridecyl myristate, and ethyl laurate, esters of a fatty acid. In particular embodiments, the plasticizer may be caprylic triglyceride. Any of the above plasticizers may be used alone or in combination (and/or in combination with any other additive mentioned herein); it will be appreciated that the above listings are exemplary and non-limiting. In some embodiments, any such plasticizer may be a hydrophobic plasticizer, meaning that it has an HLB (hydrophilic-lipophilic balance) parameter, calculated by the method of JT Davies: *A quantitative kinetic theory of emulsion type, I. Physical chemistry of the emulsifying agent, Gas/Liquid and Liquid/Liquid Interface* (Proceedings of the International Congress of Surface Activity); 426-38, 1957, of less than 10. In further embodiments, it may have an HLB parameter of less than 8, or of less than 6. It will be appreciated that any such plasticizer or plasticizers will often remain in the PSA made from the pre-adhesive composition, so as to suitably enhance the properties thereof. Moreover, such plasticizer may be added to the pre-adhesive composition; or, it may be included in the monomer mixture (reaction mixture) from which the pre-adhesive composition is made, in which case the plasticizer may serve e.g. as a non-reactive diluent.

The poly(meth)acrylate macromolecules disclosed herein can include any suitable monomer unit(s). Suitable monomer units may be chosen from various non-polar (meth)acrylate monomer units including e.g. alkyl (meth)acrylates, alkenyl (meth)acrylates, aryl (meth)acrylates, aryl substituted alkyl (meth)acrylates, aryloxy substituted alkyl (meth)acrylates, and the like.

Alkyl (meth)acrylates include, but are not limited to, methyl (meth)acrylate, ethyl (meth)acrylate, n-propyl (meth)acrylate, isopropyl (meth)acrylate, n-butyl (meth)acrylate, isobutyl (meth)acrylate, n-pentyl (meth)acrylate, isopentyl (meth)acrylate (i.e., isoamyl (meth)acrylate), 3-pentyl (meth)acrylate, 2-methyl-1-butyl (meth)acrylate, 3-methyl-1-butyl (meth)acrylate, n-hexyl (meth)acrylate, isohexyl (meth)acrylate, 2-methyl-1-pentyl (meth)acrylate, 3-methyl-1-pentyl (meth)acrylate, 4-methyl-2-pentyl (meth)acrylate, 2-ethyl-1-butyl (meth)acrylate, 2-methyl-1-hexyl (meth)acrylate, 3,5,5-trimethyl-1-hexyl (meth)acrylate, cyclohexyl (meth)acrylate, 3-heptyl (meth)acrylate, n-octyl (meth)acrylate, isooctyl (meth)acrylate, 2-octyl (meth)acrylate, 2-ethyl-1-hexyl (meth)acrylate, n-decyl (meth)acrylate, isodecyl (meth)acrylate, 2-propylheptyl (meth)acrylate, isononyl (meth)acrylate, n-dodecyl (meth)acrylate (i.e., lauryl (meth)acrylate), n-tridecyl (meth)acrylate, isotridecyl (meth)acrylate, 3,7-dimethyl-octyl (meth)acrylate, 1-octadecyl (meth)acrylate, 17-methyl-1-heptadecyl (meth)acrylate, 1-tetradecyl (meth)acrylate, and the like.

Often, such monomer units are derived from monomers that are esters of either acrylic acid or methacrylic acid with non-tertiary alcohols. Specific examples of suitable monomers may include the esters of either acrylic acid or methacrylic acid with ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. Still other suitable non-polar (meth)acrylates are aryl (meth)acrylates such as, for example, phenyl (meth)acrylate or benzyl (meth)acrylate; alkenyl (meth)acrylates such as, for example, 3,7-dimethyl-6-octenyl-1 (meth)acrylate and allyl (meth)acrylate; and aryl substituted alkyl (meth)acrylates or aryloxy substituted alkyl (meth)acrylates such as, for example, 2-biphenylhexyl (meth)acrylate, benzyl (meth)acrylate, and 2-phenoxy ethyl (meth)acrylate. It will be understood that all of the above listings are exemplary and are non-limiting.

In some embodiments, the monomer units and poly(meth)acrylate macromolecules formed therefrom may be chosen from those monomer units and macromolecules described in U.S. Pat. No. 8,137,807 to Clapper, which is incorporated by reference in its entirety herein. In embodiments in which the pre-adhesive composition is to be photo-crosslinked to form the pressure-sensitive adhesive, the pre-adhesive composition may include photo-activatable crosslinkers provided by monomer units such as e.g. acryloylethoxybenzophenone, as discussed in detail later herein.

In many embodiments, it may be convenient that at least some of the monomer units be alkyl (meth)acrylate monomer units (many of which are included among the above exemplary listings). The size of the alkyl group (e.g., the number of carbon atoms thereof) may be chosen as desired. Particularly convenient alkyl (meth)acrylate monomers may include e.g. 2-ethylhexyl acrylate and isooctyl acrylate, both of which have an alkyl group with eight carbon atoms. In some embodiments, some or all of the poly(meth)acrylate macromolecules may be homopolymers; i.e., they may consist essentially of one particular type of monomer unit (as exemplified by the isooctyl acrylate homopolymers of the Working Examples). In other embodiments, various monomer units may be copolymerized with one or more different monomer units, as desired. In various embodiments, poly(meth)acrylate copolymer macromolecules may be random copolymers, or block copolymers.

In particular embodiments, some small amount of a high-$T_g$ monomer unit (i.e., with a nominal $T_g$ of at least about minus 20° C.) may be included in the poly(meth)acrylate macromolecules, e.g. in order to adjust the $T_g$ (while remaining within the desired range disclosed herein). In various embodiments, such high-$T_g$ monomers, if present, may exhibit a nominal $T_g$ that is e.g. at least 0° C., at least 25° C., at least 30° C., at least 40° C., or at least 50° C. (It will be appreciated that when incorporated into the disclosed poly(meth)acrylate macromolecules e.g. at a few wt. %, such monomers will not exhibit this nominal $T_g$; rather, the nominal $T_g$ will be understood to be that of the high-$T_g$ monomer when polymerized by itself to form a homopolymer.) Suitable high $T_g$ monomers include, but are not limited to, methyl methacrylate, tert-butyl methacrylate, ethyl methacrylate, n-propyl methacrylate, isopropyl methacrylate, isobutyl methacrylate, tert-butyl methacrylate, stearyl methacrylate, phenyl methacrylate, cyclohexyl methacrylate, isobornyl (meth)acrylate, benzyl methacrylate, 3,3,5-trimethylcyclohexyl acrylate, cyclohexyl methacrylate, or combinations thereof.

It has been found that a high level of polar monomer units can disadvantageously affect the skin-adhesion properties of the herein-disclosed PSA. By definition, the poly(meth)acrylate macromolecules of the pre-adhesive composition include less than about 4.0 wt. % of polar monomer units. In various embodiments, the poly(meth)acrylate macromolecules include less than about 3.0, 2.0, 1.0, 0.6, 0.4, 0.2, or 0.1 wt. % of polar monomer units. In particular embodiments, the poly(meth)acrylate macromolecules are substantially free of polar monomer units, meaning that they include less than about 0.05 wt. % of polar monomer units. Polar monomer units that are subject to such exclusions include, but are not limited to, the monomer units described in PCT International Publication Number WO2013/048735 to Lewandowski, on page 6 line 27 through page 7 line 31. In specific embodiments, the poly(meth)acrylate macromolecules are substantially free of (meth)acrylic acid monomer units, of acrylamide monomer units, of acrylonitrile monomer units, of 2-hydroxyethyl acrylate monomer units, and/or of glycidyl methacrylate monomer units.

In further embodiments, a PSA as disclosed herein may include less than about 4.0, 3.0, 2.0, 1.0, 0.6, 0.4, 0.2, or 0.1 wt. % of total hydrophilic additives, whether such an additive or additives are in the form of e.g. plasticizers, tackifiers, surfactants, wetting agents, thickeners, and so on. In this context, by hydrophilic is meant a material that exhibits an HLB parameter, calculated by the Davies method, of 10 or greater.

In some embodiments, the poly(meth)acrylate macromolecules may include (meth)acrylate monomer units that comprise vinyl (olefinic) functional groups. Such monomer units may be incorporated into the poly(meth)acrylate macromolecules by virtue of their (meth)acrylate groups reacting e.g. in the initial synthesis reaction to make the pre-adhesive composition. The vinyl functional groups may remain unreacted during this initial reaction and may thus be available to enhance a subsequent cross-linking process that is used to transform the pre-adhesive composition into a PSA. For example, such vinyl functional groups (present e.g. as pendant groups of a (meth)acrylate-derived backbone of the macromolecules) may allow e.g. ebeam crosslinking to be performed with a reduced ebeam dosage. A non-limiting list of monomers that may be suitable for including vinyl groups or the like in this manner includes e.g. dicyclopentenyloxyethyl acrylate, allyl (meth)acrylate, allyl (meth) acrylamide, N,N-diallyl acrylamide, cinnamoyl (meth)acrylate, crotyl acrylate, undecenoyl (meth)acrylate, vinyl (meth)acrylate, 3-butenyl (meth)acrylate, citronelyl (meth)acrylate, geranoyl (meth)acrylate, linaloyl (meth)acrylate, isopropenyl (meth)acrylate, butadiene (meth)acrylate, O-eugenyl (meth) acrylate, allylphenyl (meth)acrylate, allyloxyethnoyl (meth) acrylate, vinyloxyethyl (meth)acrylate, diethylene glycol monoallyl ether (meth)acrylate, abitol (meth)acrylate, cholesterol (meth)acrylate, poly(butadienyl) (meth)acrylate oligomer, and poly(isoprenyl) (meth)acrylate oligomer. In some embodiments, the (meth)acrylate ester monomer is the ester of (meth)acrylic acid with allyl alcohol or 10-undecen-1-ol or a combination thereof, although combinations of two or more different (meth)acrylate ester monomer are suitable. In some embodiments, the (meth)acrylate ester monomer is the ester of (meth)acrylic acid with an alcohol derived from a renewable sources, such as citronellol, and geraniol. Any such monomers or combinations of monomers may be present in amounts of 0 to 10 parts by weight, e.g. 1 to 5 parts by weight, based on 100 parts by weight total monomer(s).

Small amounts of other (e.g., non-(meth)acrylate) monomer units may also be included in the poly(meth)acrylate macromolecules, as long as they do not unacceptably affect the properties of the pre-adhesive composition or the PSA made therefrom. Thus, in some embodiments the poly(meth)acrylate macromolecules may be copolymers that further include one or more other vinyl monomer units such as vinyl esters (e.g., vinyl acetate and vinyl propionate); styrene or derivatives thereof such as alkyl substituted styrene (e.g., alpha-methyl styrene); vinyl halides; or mixtures thereof. If present, these other vinyl monomer units can be present in any suitable amount. In some embodiments, the vinyl monomer units are present in an amount of up 5, 2, 1, or 0.5 wt. % of the poly(meth)acrylate macromolecules. However, in some embodiments the poly(meth)acrylate macromolecules are substantially free of non-(meth)acrylate vinyl monomer units. In particular embodiments, the poly(meth)acrylate macromolecules may be comprised of at least about 90, 95, 98, 99, 99.5, or 99.8 wt. % nonpolar alkyl (meth)acrylate monomer units that do not include any heteroatoms.

In various embodiments the poly(meth)acrylate macromolecules may make up at least about 60, 80, 90, 95, 98, 99, 99.5, or 99.8 wt. % of the macromolecular components (e.g., those components with an average molecular weight of over 2000) of the pre-adhesive composition. In further embodiments, the poly(meth)acrylate macromolecules may make up at least about 60, 80, 90, 95, 98, 99, 99.5, or 99.8 wt. % of the total components of the pre-adhesive composition. In some embodiments, the pre-adhesive composition (and the PSA made therefrom) can include optional components such as, for example, pigments, glass beads, polymer beads (e.g., expandable beads or expanded beads), mineral fillers such as e.g. silica, calcium carbonate, and the like, fire retardants, antioxidants, and stabilizers and so on. In some embodiments, the pre-adhesive composition (and the PSA made therefrom) can include one or more hydrocolloids (e.g., carboxymethyl cellulose, gelatin, pectin, croscarmellose sodium, and the like). In various embodiments, such a hydrocolloid or hydrocolloids can be present (in total) at least at about 0.5, 1, 5, or 10 wt. % of the PSA. In further embodiments, such a hydrocolloid or hydrocolloids can be present (in total) at most at about 35, 25, or 15 wt. % of the PSA Any of these optional components can be added in any amount sufficient to obtain the desired properties, as long as they do not unacceptably interfere with the properties and functioning of the pre-adhesive composition and the PSA made therefrom. In general, with respect to polar components (including not only the previously-discussed polar monomer units, but also e.g. any hydrocolloids, plasticizers, fillers, thickeners, wetting agents, and so on, that may be polar in nature), the pre-adhesive composition and the PSA made therefrom may, in various embodiments, have polar components that are present (in total) at less than about 5, 2, 1, 0.5, 0.2, 0.1, 0.05, or 0.01% wt. %.

In some embodiments, the pre-adhesive composition (and the PSA made therefrom) can optionally include at least one tackifier. Suitable tackifiers and amounts in which they may be present in a PSA are discussed in detail in PCT International Publication Number WO2013/048735 to Lewandowski, on page 13 line 22 through page 15 line 12. In particular embodiments the pre-adhesive composition includes less than about 2, 1, 0.4, 0.2, or 0.1 wt. % tackifier.

In some embodiments, the pre-adhesive composition (and the PSA made therefrom) can optionally include any suitable antimicrobial agent, disinfectant, bactericide, preservative, or the like.

Methods of Making

In general, the methods disclosed herein include at least the crosslinking of a pre-adhesive composition comprised of poly(meth)acrylate macromolecules that comprise a number-average molecular weight of from about 25000 to about 200000, to form a pressure-sensitive adhesive. In at least some embodiments, the methods also include a first, synthesis reaction in which a first, monomer mixture (reaction mixture) comprising (meth)acrylate monomers is polymerized to form the poly(meth)acrylate macromolecules of the pre-adhesive composition. (The term "monomer mixture" is used for convenience and it will be understood that such a mixture is not limited to monomers but rather may include e.g. one or more of initiators, chain transfer agents, solvents, plasticizers, and so on).

A first, synthesis reaction to form at least the poly(meth) acrylate macromolecules of the pre-adhesive composition can be carried out in any suitable manner. For example, desired amounts of one or more (meth)acrylate monomers (as described above) may be placed into a reaction vessel, along with any desired initiator, solvent, and the like, and the synthesis reaction carried out. Suitable initiators may include e.g. any thermal initiator, photoinitiator, or both, and can be present in any suitable amount.

Suitable thermal initiators may be chosen e.g. from well-known peroxides and/or from aliphatic azo compounds such as e.g. azobisisobutyronitrile (AIBN) and derivatives thereof (many such thermal initiators are available from DuPont under the trade designation VAZO). Suitable photoinitiators may be chosen from e.g. products available from Ciba under the trade designation IRGACURE. Further details of various thermal initiators and photoinitiators that may be used in the polymerization of (meth)acrylate and like monomers are discussed in PCT International Publication Number WO2013/048735 to Lewandowski, on page 11 line 21 through page 12 line 19.

If a thermal initiator is used, the first, synthesis reaction may be initiated e.g. by heating the reaction mixture to a temperature sufficient to activate the thermal initiator. If a photoinitiator is used, the reaction mixture may be exposed to e.g. UV or visible light using any suitable photo-irradiation source (e.g., UV-bulbs and the like). As will be appreciated from the Examples herein, the amount of initiator used (e.g. in relation to the amount of polymerizable monomer present) may affect the degree of polymerization/molecular weight of the resulting poly(meth)acrylate macromolecules and thus the amount of initiator may thus be conveniently used as a result-effective variable to affect those parameters.

In some embodiments, the monomer mixture (reaction mixture) for the first, synthesis reaction may include at least one chain transfer agent. As will be evident from the Examples herein, a chain transfer agent can be used to help control the degree of polymerization/molecular weight of the resulting poly(meth)acrylate macromolecules as desired. Examples of useful chain transfer agents include, but are not limited to, carbon tetrabromide, alcohols, mercaptans such as isooctylthioglycolate, and mixtures thereof. If a chain transfer agent is used, the reaction mixture may include up to 0.5 weight percent of a chain transfer agent based on the total weight of polymerizable material. In various embodiments, the reaction mixture for the first, synthesis reaction can contain 0.01 to 0.5 weight percent, 0.05 to 0.5 weight percent, or 0.05 to 0.2 weight percent chain transfer agent. It will be appreciated that if a chain transfer agent is used, at least some of the poly(meth)acrylate macromolecules may exhibit at least one chain transfer agent residue (with the term "residue" denoting a moiety of the macromolecule that is identifiable as having come from a chain transfer agent).

In some embodiments, the reaction mixture for the first, synthesis reaction can optionally contain any suitable amount of organic solvent. In various embodiments, the reaction mixture may comprise less than 2, 1, 0.4, 0.2, or 0.1 wt. % solvent (based on the total weight of the reaction mixture). In some embodiments, the reaction mixture for the first, synthesis reaction may be substantially free of organic solvent. If an organic solvent is used, it may be chosen from any suitable solvent, e.g. methanol, tetrahydrofuran, ethanol, isopropanol, heptane, acetone, methyl ethyl ketone, methyl acetate, ethyl acetate, toluene, xylene, and ethylene glycol alkyl ether. Such solvents can be used alone or as mixtures thereof. If present, a solvent may remain in the pre-adhesive composition to facilitate further processing (e.g. to reduce the viscosity to facilitate e.g. coating the composition onto a substrate); or, the solvent may be removed after the polymerization is complete so that the resulting pre-adhesive composition has a reduced amount of solvent (e.g. may be substantially free of organic solvent). As noted earlier, one or more plasticizers may also be included in the pre-adhesive composition, and may similarly serve to reduce the viscosity of the pre-adhesive mixture (while remaining in the final PSA product rather than being removed after coating in the manner of a solvent).

The pre-adhesive compositions as disclosed herein, comprising poly(meth)acrylate macromolecules of unconventionally low molecular weight, may advantageously comprise relatively low viscosities (e.g. at 25° C.). This may allow at least some such compositions to be coated even at a very low solvent content, or even e.g. when the composition is substantially free of solvent. While in some cases such coating might be done at room temperature, in other cases the composition might be heated (e.g. in the manner of a hot-melt coating composition) to facilitate the coating operation. In various embodiments, the pre-adhesive composition may exhibit an average viscosity of no more than about 4000, 1600, 800, 400, 200, 100, 50, 20, or 10 Pa's at 25° C. In further embodiments, any of these viscosities may be exhibited by a pre-adhesive composition that is substantially free of solvent.

In some embodiments, reaction mixtures, conditions, and procedures may be employed that allow the first, synthesis reaction to be performed in an environment that uses a lower amount of solvent (e.g. volatile solvent) or may even be substantially free of such solvent. Such approaches may use e.g. the general methods and compositions discussed in U.S. Pat. Nos. 5,637,646, 5,753,768, 5,986,011, 7,691,437 and 7,968,661 to Ellis, and in PCT Published Application WO2014/078123 to Kurian, all of which are incorporated by reference herein. If desired, a non-reactive diluent (e.g. a non-volatile plasticizer) may however be present. Moreover, even if the pre-adhesive mixture is made in a solventless environment, some (e.g. small) amount of solvent may be added to the pre-adhesive composition e.g. to facilitate coating the composition on a substrate if desired. As defined herein, a solventless composition (e.g., a reaction mixture, a coating mixture, or, specifically, a pre-adhesive composition) is a composition that comprises less than about 0.2% by weight of any volatile solvent (which category does not include e.g. plasticizers, chain-transfer agents, initiators, processing aids, or any other ingredient that remains in the final PSA product).

The pre-adhesive composition may be disposed on (e.g., coated on) any suitable substrate (e.g., backing) and cross-linked to transform the pre-adhesive composition into a PSA. The pre-adhesive composition can be coated using any conventional coating techniques modified as appropriate to the particular substrate. For example, the composition can be applied to a variety of substrates by methods such as roller coating, flow coating, dip coating, spin coating, spray coating, knife coating, and die coating. The resulting PSA may have any suitable thickness (e.g., final thickness, after crosslinking, and removal of any solvent if present). In some embodiments, the thickness of the pressure-sensitive adhesive layer is at least 12 µm or at least 25 µm. In various embodiments, the pressure-sensitive adhesive layer has a thickness no greater than 1200 µm, 500 µm, 250 µm, 125 µm, 100 µm, 75 µm, or 50 µm. In particular embodiments in which the coated pre-adhesive layer is crosslinked by photo-irradiation (as discussed below), it may be advantageous to coat the layer at a (dry) coating thickness of no more than about 50, 40, 30, or 20 microns.

As disclosed herein, the pre-adhesive composition is crosslinked (in a second, crosslinking reaction) to form a pressure-sensitive adhesive. Often, it is convenient to perform such crosslinking on the pre-adhesive composition after it has been coated as a layer onto a major surface of a desired substrate as noted above. It has been found that crosslinking of the herein-disclosed pre-adhesive composition (specifically, of the poly(meth)acrylate macromolecules thereof) can result in a pressure-sensitive adhesive that is extremely gentle to human skin and yet that has sufficient cohesive strength and other properties to function well as a pressure-sensitive adhesive for e.g. skin-bonding applications. The extent of crosslinking can be characterized by the gel content (percent gel) of the pressure-sensitive adhesive. (As obtained as described in the Examples herein, the gel content is a measure of the insoluble (networked) polymeric material that remains after extraction of soluble content). In various embodiments, the gel content of pressure-sensitive adhesive obtained from crosslinking of the poly(meth)acrylate macromolecules of the pre-adhesive composition, may be at least about 10, 20, 30, 40, or 50%. In further embodiments, the gel content of the pressure-sensitive adhesive may be at most about 90, 80, 70, or 65%. (It will be understood that gel content is a characterization of the macromolecular components of a composition and that in particular embodiments in which solvent, plasticizer, and so on, are present in the reaction product (e.g., in the PSA product), such components will be not be included in assessing gel content.)

In some embodiments, it may be convenient to perform the crosslinking by electron beam (ebeam). The ebeaming may be performed using any suitable apparatus, as are widely available. The ebeaming may be performed at any suitable conditions, e.g. combination of operating voltage (e.g., in kV) and dose (e.g., in Megarads). The ordinary artisan will appreciate that ebeaming is a mode of crosslinking in which high energy electrons interact with molecules in a generally non-specific manner to generate e.g. free radicals that may then form covalent bonds with other macromolecules. It will be thus be understood that such methods fall into a first general class of PSA production methods in which a crosslinking reaction is triggered in a non-specific manner (e.g. by a high energy electron) that may activate a macromolecule for crosslinking at any location along the macromolecular chain and that may not necessarily leave a specific residue (chemical signature) at the crosslink site. It will be appreciated that the use of ebeam to promote the second, crosslinking reaction can allow any suitable initiation mechanism (e.g., thermal initiation or photo-initiation) to be used to initiate the first, synthesis reaction.

In some embodiments, it may be convenient to perform the crosslinking of the pre-adhesive composition by photo-crosslinking. Such approaches involve photo-irradiating the pre-adhesive composition with (non-ionizing) electromagnetic radiation in a wavelength range of e.g. 100-500 nm (such processes are often referred to e.g. as UV-curing, light-curing, and so on). This may be performed using any suitable apparatus (as are widely available), and may be performed at any suitable conditions, e.g. combination of wavelength, dose rate, and so on.

To facilitate such approaches, the pre-adhesive composition (specifically, the macromolecules that make up the pre-adhesive composition) may include one or more photo-crosslinkers. This may be conveniently achieved by including one or more photo-crosslinkers (by which is meant a molecule that includes both a photo-activatable moiety and a (meth)acrylate moiety) in the monomer mixture used in the first, synthesis reaction to make the pre-adhesive composition. Such molecules may thus be incorporated (by way of their (meth)acrylate functionality) into the macromolecular chains of the pre-adhesive composition during the first, synthesis reaction. The pre-adhesive composition may then be coated as a layer onto a suitable substrate. The photo-activatable moieties of at least some of the photo-crosslinker molecules may then be activated by photo-irradiating the coated layer. This will generate e.g. free radicals that may then form covalent bonds with other macromolecules so as to crosslink the pre-adhesive composition to form a pressure-sensitive adhesive.

In contrast to the non-specific generation of free radicals that typically results from impinging high energy electrons onto macromolecules, in photo-irradiation the initiation of a free radical will typically occur specifically by decomposition of the photo-activatable moiety of the photo-crosslinker. It will thus be understood that photo-irradiation methods fall into a second general class of PSA production methods in which a crosslinking reaction is triggered by activation of a specific functional entity (e.g., the photo-activatable moiety of the photo-crosslinker). That is, a specifically identifiable residue (chemical signature) of a photo-activatable crosslinker may be observable in the macromolecules of the product PSA—for example, if the photo-activatable crosslinker is e.g. a benzophenone, the macromolecules of the resulting pressure-sensitive adhesive may exhibit detectable benzophenone residues.

Any suitable photo-activatable crosslinker may be used, as provided e.g. by way of any molecule that has dual functionality provided by a (meth)acrylate polymerizable moiety and a photo-activatable moiety. One such suitable molecule is acryloylethoxybenzophenone. Other potentially suitable molecules may include e.g. methacryloylethoxybenzophenone, acryloylbenzophenone, and methacryloyl-benzophenone. Any such photo-activatable crosslinker may be provided in the reaction mixture used in the first, synthesis reaction, in any suitable amount. In particular embodiments, the photo-activatable crosslinker may be present at no more than about 1.2, 1.0, 0.8, 0.6, 0.4, or 0.2 wt. %, based on the total weight of the acrylate polymerizable monomers in the first, synthesis reaction mixture. In further embodiments, the photo-activatable crosslinker may be present at least at about 0.05, 0.1, 0.15, 0.2, or 0.3 wt. %.

It will also be understood that when a pre-adhesive composition is to be photo-crosslinked, it may be advantageous to initiate the first, synthesis reaction in some other way than by photo-initiation (for example, the first, synthesis reaction could be thermally initiated). This can help to minimize any chance of a photo-activatable crosslinker being activated prematurely, during the first synthesis reaction.

Pre-adhesive compositions, methods of making such compositions, and methods of preparing PSAs and PSA-containing articles from such compositions, are discussed in PCT application number US2015/017489, entitled Gentle to Skin (Meth)Acrylate Pressure-Sensitive Adhesive, filed 25 Feb. 2015, which is incorporated by reference in its entirety herein.

A pre-adhesive composition as disclosed herein can be disposed on (e.g. coated on) a major surface of any suitable substrate and crosslinked to provide a pressure-sensitive adhesive (PSA) layer as described above. In some embodiments, such a substrate may be a tape backing upon which the coated layer (after crosslinking as described below) will remain as a PSA attached thereto. If the back surface of the tape backing has release properties, the tape may be provided in the form of a self-wound roll.

In more general terms, a pre-adhesive composition as disclosed herein can be disposed on any substrate, e.g. in a continuous or discontinuous manner, and crosslinked so as to provide an article comprising the resulting PSA. In at least some embodiments such an article may be provided in the form of a discrete article (whether as-made, or by converting from a continuous substrate such as a precursor roll good) rather than as a roll good. This being the case, the use herein of the word tape is done for convenience and does not require that the "tape" must take the form of a roll good. Suitable substrates (e.g., backings) include, but are not limited to, polymeric films such as those prepared from polypropylene, polyethylene, polyvinyl chloride, polyester (polyethylene terephthalate or polyethylene naphthalate), polycarbonate, polymethyl(meth)acrylate (PMMA), cellulose acetate, cellulose triacetate, and ethyl cellulose. Such films may be solid, or may comprise at least some level of porosity. In some embodiments, a porous substrate may be a fibrous substrate, e.g. a non-woven web, a paper backing, a woven or cloth backing, and so on. In some embodiments, a backing may be comprised of foam (which foam may be e.g. an open-cell foam or a closed cell foam). The pre-adhesive composition may be coated e.g. essentially continuously onto a major surface of the substrate (except for such e.g. coating imperfections as may occasionally occur in coating operations, as will be well understood by the ordinary artisan); or the pre-adhesive composition may be discontinuously coated, e.g. pattern coated, onto the major surface of the substrate. The pre-adhesive composition may be coated directly onto a major surface of the substrate; or, one or more primer coatings, tie layers, or the like may be provided.

In some embodiments, the substrate onto which the pre-adhesive composition is coated may be a release liner, so that a liner/PSA stack is formed. In such a case, the major surface of the PSA opposite the release liner may then be contacted with (bonded to) a tape backing to form an adhesive tape (with the release liner being removable during use of the tape). Such a product might be provided as a roll of adhesive tape or as discrete lengths of adhesive tape. In some embodiments, the substrate onto which the pre-adhesive composition is coated may be a sacrificial substrate (e.g. a temporary carrier) onto which the composition is coated (and e.g. crosslinked) and from which the resulting PSA is then transferred to a tape backing.

Compositions disclosed herein may display advantageous properties (e.g., gentle release from skin, and/or the ability to be debonded from e.g. skin and rebonded thereto with minimal loss of pressure-sensitive adhesive properties) while relying on relatively inexpensive materials such as (meth)acrylates (and e.g. plasticizer, if present). Compositions disclosed herein may also exhibit satisfactory, or even excellent, moisture-vapor transmission even while containing little or no polar monomer units and/or additives. While applications such as bonding to skin, e.g. human skin, are discussed herein, and the compositions disclosed herein exhibit properties that make them particularly advantageous for such uses, it will be understood that these are non-limiting examples and that the pre-adhesive compositions disclosed herein, the PSAs made therefrom, can be used for any desired application, whether in the areas of consumer use, industrial use, or elsewhere. Furthermore, such compositions are not limited to being made by the particular exemplary methods disclosed herein (e.g. a first, synthesis reaction of the particular type described above).

Adhesion to Wet Surfaces

It has been found that PSAs derived from the pre-adhesive compositions described herein can exhibit enhanced adhesion to wet or moist surfaces. Such properties can render these PSAs particularly suitable applications in which there is a need to bond to wet surfaces. Furthermore, such properties can render these PSAs suitable for use in moist or high-humidity environments in which even though a surface to be bonded may not necessarily exhibit visible water thereon, the surface may still have sufficient surface condensation thereon to cause the bonding achieved by a conventional PSA to be poor. A non-limiting list of applications in which the present adhesives may find use thus includes masking tapes (e.g., outdoor masking tapes), tapes used in outdoor construction, tapes used in moist or damp environments such as e.g. washrooms, locker rooms and so on, and tapes used in marine or boating applications. Even such conventional uses as e.g. box sealing tapes might benefit from use of the present adhesives, since such adhesives may be occasionally called on to seal a box upon which some liquid water may have been e.g. accidentally spilled. Moreover, not all such uses need be in the form of roll goods such as tapes. Rather, the herein-disclosed PSAs may be used in discrete articles such as e.g. stretch-release double-faced adhesive articles, particularly if such articles may find use in high-humidity environments.

It has also been found that the herein-described adhesives are particularly suitable for bonding to wet skin, e.g. wet human skin. Such a property may render the adhesives suitable for use in (but is not limited to) e.g. medical tapes, athletic tapes, adhesive bandages (e.g. the widely available over-the-counter bandages of the general type e.g. available from 3M Company under the trade designation NEX-CARE), wound dressings, wound closure strips (e.g., butterfly closures, steri-strips, and so on), surgical drapes, monitoring electrodes, patient grounding plates, transcutaneous electrical nerve stimulation (TENS) devices, transdermal drug-delivery devices, ostomy appliances, cannula retention dressings (e.g., for IV lines and/or arterial lines) and so on. The ability of a PSA to bond to a wet surface, e.g. wet skin, can be evaluated e.g. by way of the Wet-Stick Test Method described in the Examples herein. (The test method relies on an artificial skin substrate of the general type described e.g. in PCT Patent Application Publication WO 2011153308, which is incorporated by reference in its entirety herein.) A PSA that exhibits a Peak Pull Force of at least about 2000 g when tested in the Wet-Stick Test Method is defined herein as a "wet-stick" PSA. In various embodiments, a wet-stick PSA as disclosed herein may exhibit a Peak Pull Force of at least about 2500 g, 3000 g, 3500 g, 4000 g, or 4500 g, when so tested.

The ability of a PSA to bond to wet skin can also be evaluated by way of the Adhesion to Dry and Wet Skin Test Protocols described in columns 12 and 13 of U.S. Pat. No. 6,518,343 to Lucast, which portion thereof is incorporated by reference herein for this specific purpose. A parameter that can be obtained by these Test Protocols is an initial skin adhesion ($T_o$) to wet skin, reported in Newtons per decimeter. In various embodiments, a PSA as disclosed herein may exhibit an initial skin adhesion to wet skin of at least about 0.8, 1.6, 2.0, 3.0, or 4.0 N/dm.

The advantageous ability of the herein-disclosed PSAs to exhibit wet stick, as evidenced in the Working Examples herein, is unexpected in view of the fact that these PSAs do not require the presence of polar components in order to exhibit excellent wet stick. It has conventionally been thought that (meth)acrylate polymers that are hydrophobic in nature are generally unsuitable as wet-stick adhesives (as evidenced by e.g. the discussions in the Background sections of U.S. Pat. Nos. 6,518,343 and 6,441,092) unless modified to increase their hydrophilic character. In the present work, excellent wet stick adhesion has been demonstrated with representative PSAs based on e.g. 95 wt. % poly(ethylhexyl acrylate) and 5 wt. % caprylic triglyceride plasticizer. The ordinary artisan will consider that poly(ethylhexyl acrylate) is a quintessential hydrophobic acrylate and will consider caprylic triglyceride to be a relatively hydrophobic plasticizer (having an HLB value, calculated by the Davies method, of approximately 5). Therefore, the ordinary artisan would view the tested samples as being prototypical examples of a PSA based on a hydrophobic (meth)acrylate composition, and would thus view the excellent wet stick properties exhibited by these PSAs as being unexpected based on the teachings in the art.

The ordinary artisan would thus appreciate that the herein-disclosed PSAs can provide (meth)acrylate PSAs with enhanced wet-stick properties, without necessarily requiring the inclusion of significant amounts of hydrophilic moities (whether added in the guise of e.g. hydrophilic (meth)acrylate monomer units that are incorporated into the macromolecular chains, and/or by way of additives such a e.g. hydrophilic surfactants, hydrophilic polymers, and the like). Furthermore, the ordinary artisan, having background knowledge of PSAs and of potential components thereof such as plasticizers, tackifiers, and so on, would expect that the effect of a hydrophobic plasticizer such as e.g. caprylic triglyceride would be to e.g. slightly lower the $T_g$ of the composition. That is, it would not be expected that the addition of a hydrophobic plasticizer would improve the wet-stick properties of the PSA. Therefore, the ordinary artisan would believe that the effects demonstrated in the Working Examples herein would not necessarily be limited to PSAs that include a plasticizer, e.g. a hydrophobic plasticizer such as caprylic triglyceride in particular.

In one embodiment, disclosed herein is a medical tape (which may be used e.g. to secure an IV line to a patient, to attach a bandage or dressing to a patient, and so on, and may also be known as a surgical tape) comprising a PSA as described herein. In another embodiment, disclosed herein is a wound dressing comprising a PSA as described herein (such a wound dressing may optionally include one or more absorbent materials, such as e.g. a foam, gauze, or a hydrocolloid, as will be well understood by the ordinary artisan). In another embodiment, disclosed herein is a wound closure strip comprising a PSA as described herein. In another embodiment, disclosed herein is an adhesive bandage comprising a PSA as described herein. In another embodiment, disclosed herein is a surgical drape comprising a PSA as described herein. In another embodiment, disclosed herein is a cannula retention device comprising a PSA as described herein. In another embodiment, disclosed herein is an electrode (e.g., a monitoring electrode or a diagnostic electrode) comprising a PSA as described herein (such an electrode may often comprise a backing, e.g. a foam backing, bearing an annular skirt of the PSA surrounding e.g. a conductive gel pad). In another embodiment, disclosed herein is a patient grounding plate comprising a PSA as described herein. In another embodiment, disclosed herein is a transcutaneous electrical nerve stimulation (TENS) device comprising a PSA as described herein. In another embodiment, disclosed herein is a transdermal drug delivery device (e.g., patch) comprising a PSA as described herein. In another embodiment, disclosed herein is an ostomy appliance comprising a PSA as described herein.

It will be understood that the above list is non-limiting; furthermore, the ordinary artisan will appreciate that there may not necessarily be a bright-line distinction between the terminology used therein (for example, terms such as medical tape and surgical tape may be used somewhat interchangeably, as may terms such as drape and dressing and/or bandage and dressing). However, all such products and uses will share in common the use of a PSA (e.g. a wet-stick PSA) as disclosed herein, disposed on a backing (whether discrete or in the form of a roll good), e.g. along with any such ancillary device(s) or component(s) (e.g., a release liner, one or more absorbent materials, one or more conductive gels, one or more drug-delivery reservoirs, and/or wiring, tubing, vents, ports, valves, and so on) as may be helpful for functioning in a particular application. All such articles and uses are encompassed with the disclosures herein.

In some embodiments, any such article 1 (whether discrete or in the form of a roll good) can take the form of a layer of e.g. a wet-stick pressure-sensitive adhesive 10 disposed (e.g., coated) on a backing 15, as shown in exemplary representation in FIG. 1. In some embodiments, the PSA may be disposed on essentially the entire area of the backing; or, the PSA may be disposed only on a portion of the area of the backing. Backing 15 may be comprised of any suitable material, e.g. polyolefin, polyester, polyurethane, and so on (in particular, it may be comprised of materials commonly used as backings for medicals drapes or dressing, which will be familiar to the ordinary artisan). The substrate may be a single-layer substrate or a multilayer substrate, and may have particular properties (e.g., tear strength, porosity or lack thereof, transparency or opacity, surface roughness or smoothness, and so on) as may be helpful in a particular application. Backing 15 may be continuous or discontinuous (e.g., it may take the form of a cloth backing, a paper backing, a nonwoven backing, a film backing, and so on). In some embodiments backing 15 may be configured to be hand-tearable across the transverse width of the article (e.g., by providing suitable lines of weakness, e.g. in the form of perforations). In certain applications, backing 15 and PSA 10 may be sterilized (by any suitable method), and may be supplied to an end user in a sterile package. In some embodiments, backing 15 may be chosen so as to exhibit an enhanced moisture-vapor transmission rate (MVTR), whether by way of using a porous backing 15 and/or by using a backing 15 that is comprised of materials (e.g., hydrophilic polyurethanes) that, even though they may be non-porous, may exhibit relatively high MVTR. In various embodiments, backing 15 may exhibit an MVTR of from about 500-3000, 500-1500, or 1000-1500, grams water per meter squared per 24 hours, when tested according to the procedure outlines in column 12 of U.S. Pat. No. 6,121,508. In alternative embodiments, backing 15 may exhibit an MVTR of less than about 500, 400, 300, 200, 100 or 50 grams of water per meter squared per 24 hours. Any such article may optionally include a release liner 16 on a major surface of the PSA opposite the backing, which release liner can be removed for use of the article. In various embodiments, any such article 1 (particularly if used e.g. as a dressing, bandage or the like) can include any desired material that is e.g. water-absorbent, water-transmissive and/or water-wicking, or the like. Such a material may comprised e.g. one or more of hydrocolloid, gauze, fabric, an open-cell foam such as a reticulated polyurethane foam, a superabsorbent material, or the like, including combinations of any of these. In some embodiments, article 1 may include one or more active agents that can e.g. promote wound healing and/or patient comfort. Such an active agent might be e.g. an antimicrobial, antifungal, or antiviral agent, a growth factor, an anesthetic, or any combination thereof.

In some embodiments, the herein-described pressure-sensitive adhesive is the only pressure-sensitive adhesive present in or on article 1 that is configured to bond to skin in use of article 1 (one or more other PSAs may of course be present for other purposes, e.g. used to bond various parts of article 1 together in the production of article 1). In some embodiments, article 1 is bonded to skin solely by the use of the herein-described PSA, with no other adhesive tapes, trips, bandages, and so on, being used in bonding article 1 to the skin.

In specific embodiments, the PSAs disclosed herein can be used in so-called negative pressure wound therapy (NPWT) devices, such as e.g. NPWT dressings. The use of these PSAs in NPWT devices is discussed in U.S. Provisional Patent Application No. 62/212,219, filed evendate herewith and entitled NEGATIVE PRESSURE WOUND THERAPY DRESSINGS COMPRISING (METH)ACRYLATE PRESSURE-SENSITIVE ADHESIVE WITH ENHANCED ADHESION TO WET SURFACES, which is incorporated by reference in its entirety herein.

(Dry) Peel Adhesion

Certain aspects of the performance of a pressure-sensitive adhesive as disclosed herein may be characterized by way of a Peel Adhesion test (i.e., a 180° Peel Adhesion Test, measured as disclosed in the Examples herein). For such purposes the PSA may be conveniently provided on (e.g., deposited onto using e.g. methods disclosed herein) a conventional tape backing, e.g. a nonwoven backing of the general type used in the product available in 2014 from 3M Company, St. Paul Minn. under the trade designation KIND REMOVAL SILICONE TAPE. If the Peel Adhesion of an existing pressure-sensitive adhesive tape (i.e., a PSA already on a tape backing) is to be evaluated, the test may of course be performed on the adhesive tape as supplied. In various embodiments, a pressure-sensitive adhesive and/or a pressure-sensitive adhesive tape as disclosed herein may exhibit a Peel Adhesion of at most about 400, 300, 240, or 200 grams per inch. In further embodiments, a pressure-sensitive adhesive and/or a pressure-sensitive adhesive tape as disclosed herein may exhibit a Peel Adhesion of at least about 50, 100, 140, or 180 grams per inch. In at least some embodiments, a pressure-sensitive adhesive and/or a pressure-sensitive adhesive tape as disclosed herein will not exhibit cohesive failure during a Peel Adhesion test. The ordinary artisan will understand this to mean that the adhesive layer will part (debond) from the test substrate at the interface between the adhesive layer and the test substrate rather than the adhesive layer splitting or otherwise leaving significant residue behind on the test substrate. (In other words, the ordinary artisan will appreciate that the debonding occurs by way of separation of the surface of the adhesive layer from the surface of the test substrate and will thus appreciate that the condition that cohesive failure does not occur, may alternatively be phrased that the PSA exhibits "interfacial debonding" in a Peel Adhesion test).

LIST OF EXEMPLARY EMBODIMENTS

Embodiment 1 is a wet-stick pressure-sensitive adhesive article, comprising: a substrate bearing on a major surface thereof a wet-stick pressure-sensitive adhesive, wherein the wet-stick pressure-sensitive adhesive is the crosslinking reaction product of a pre-adhesive composition comprising poly(meth)acrylate macromolecules that comprise a number-average molecular weight of from about 25000 to about 200000, and wherein the pre-adhesive composition exhibits a $T_g$ of less than about minus 20° C. and exhibits a storage modulus of from about 4 Pa to about 10000 Pa at 25° C.

Embodiment 2 is the adhesive article of embodiment 1 wherein the poly(meth)acrylate macromolecules of the pre-adhesive composition comprise a number-average molecular weight of from about 25000 to about 100000. Embodiment 3 is the adhesive article of embodiment 1 wherein the poly(meth)acrylate macromolecules of the pre-adhesive composition comprise a number-average molecular weight of from about 25000 to about 40000. Embodiment 4 is the adhesive article of any of embodiments 1-3 wherein the pre-adhesive composition exhibits a storage modulus of from about 100 Pa to about 1000 Pa. Embodiment 5 is the adhesive article of any of embodiments 1-4 wherein the pre-adhesive composition exhibits a viscosity from about 10 Pa's to about 800 Pa's at 25° C.

Embodiment 6 is the adhesive article of any of embodiments 1-5 wherein the poly(meth)acrylate macromolecules make up at least about 95 wt. % of the macromolecular components of the pre-adhesive composition. Embodiment 7 is the adhesive article of any of embodiments 1-6 wherein the poly(meth)acrylate macromolecules consist essentially of nonpolar (meth)acrylate monomer units with a $T_g$ of less than 0° C. Embodiment 8 is the adhesive article of any of embodiments 1-7 wherein the poly(meth)acrylate macromolecules consist essentially of alkyl (meth)acrylate monomer units. Embodiment 9 is the adhesive article of any of embodiments 1-8 wherein the poly(meth)acrylate macromolecules of the pre-adhesive composition are substantially linear macromolecules.

Embodiment 10 is the adhesive article of any of embodiments 1-9 wherein the wet-stick pressure-sensitive adhesive exhibits a Peak Pull Force of at least about 3000 g when tested according to the Wet-Stick Test Method. Embodiment 11 is the adhesive article of any of embodiments 1-10 wherein the wet-stick pressure-sensitive adhesive includes from about 2 wt. % to about 10 wt. % of a plasticizer, based on the total weight of the wet-stick pressure-sensitive adhesive. Embodiment 12 is the adhesive article of any of embodiments 1-11 wherein the poly(meth)acrylate macromolecules are the reaction product of a first, synthesis reaction of a monomer mixture that included at least one chain transfer agent and wherein at least some of the poly(meth)acrylate macromolecules include at least one chain transfer agent residue. Embodiment 13 is the adhesive article of any of embodiments 1-12 wherein the pressure-sensitive adhesive exhibits a gel content of from about 40 to about 70%.

Embodiment 14 is the adhesive article of any of embodiments 1-13 wherein the pressure-sensitive adhesive is an e-beam crosslinking reaction product of the pre-adhesive composition. Embodiment 15 is the adhesive article of any of embodiments 1-13 wherein the pressure-sensitive adhesive is a photo-crosslinking reaction product of the pre-adhesive composition and wherein at least some of the poly(meth)acrylate macromolecules of the crosslinked reaction product include at least one photo-activatable crosslinker residue.

Embodiment 16 is the adhesive article of any of embodiments 1-15 wherein the adhesive article is chosen from the group consisting of a medical tape, an adhesive bandage, a wound dressing, a wound closure strip, a surgical drape, and a cannula retention device. Embodiment 17 is the adhesive article of any of embodiments 1-15 wherein the adhesive article is chosen from the group consisting of a monitoring or diagnostic electrode, a patient grounding plate, a transcutaneous electrical nerve stimulation device, a transdermal drug delivery device, and an ostomy appliance. Embodiment 18 is the adhesive article of any of embodiments 1-17 with the proviso that the adhesive article does not comprise any pressure-sensitive adhesive other than the wet-stick pressure-sensitive adhesive.

Embodiment 19 is a method of bonding a wet-stick pressure-sensitive adhesive article to skin, the method comprising applying the pressure-sensitive adhesive of the pressure-sensitive adhesive article of any of embodiments 1-18 to skin. Embodiment 20 is the method of embodiment 19 with the proviso that no pressure-sensitive adhesive other than the pressure-sensitive adhesive of any of embodiments 1-18 is used to bond the pressure-sensitive article to the skin.

EXAMPLES

Materials

Table 1 contains a glossary of raw materials and reagents used. All parts and percentages disclosed herein are on a weight basis, unless otherwise indicated.

TABLE 1

| | |
|---|---|
| IOA | Isooctyl acrylate, monomer; available from Sigma-Aldrich (St. Louis, MO) |
| EHA | 2-Ethyl hexyl acrylate, monomer; available from Sigma-Aldrich (St. Louis, MO) |
| DDA | Dodecylacrylate, monomer, obtained from 3M Company |
| EtOAc | Ethyl acetate, solvent; available from VWR (Radnor, PA) |
| IRG651 | 2-dimethoxy-2-phenylacetophenone, photoinitiator, available from BASF (Florham Park, NJ) under the trade designation IRGACURE 651 |
| VA67 | 2,2'-azobis-(2-methylbutyronitrile); thermal initiator, available from DuPont (Wilmington, DE) under the trade designation VAZO 67 |
| AeBP | Acryloylethoxybenzophenone; photocrosslinker, obtained from 3M Co. St. Paul, MN |
| IOTG | Isooctyl thioglycolate, chain transfer agent; available from Sigma-Aldrich (St. Louis, MO) |
| CTG | Caprylic triglyceride, plasticizer; available from Croda Inc. (Edison, NJ) |
| CMC | Carboxymethylcellulose, obtained from AMTEX, Lombard, IL, under the trade designation GELYCEL |

Test Methods

Molecular Weights

Number-average molecular weights ($M_n$) and weight-average molecular weights ($M_w$) were obtained by conventional gel permeation chromatography against EasiCal polystyrene molecular weight standards (Agilent Technologies, Santa Clara, Calif., USA) using tetrahydrofuran as solvent and mobile phase. The equipment consisted of an Agilent 1100 (Pump, degasser, autosampler, column oven, differential refractive index detector) (Agilent Technologies, Santa Clara, Calif., USA) operating at 40° C. and flow rate of 1.0 mL/min. The stationary phase consisted of a Jordi Gel DVB Mixed column (250 mm×10 mm ID) (Jordi Labs, Mansfield, Mass., USA). Molecular weight calculations were performed using Cirrus GPC software from Polymer Labs (now Agilent Technologies, Santa Clara, Calif., USA). The degree of polymerization (DP) of a macromolecule was obtained by dividing $M_n$ by the molecular weight of the monomer unit (e.g., 184 g/mole for isooctyl acrylate monomer units); contributions of e.g. initiator, crosslinker and/or chain transfer agent were neglected.

Dynamic Mechanical Analysis (DMA)

DMA was used to measure the storage modulus, viscosity, and glass transition temperatures of pre-adhesive compositions. A small sample of pre-adhesive composition was transferred onto the bottom plate of a rheometer (obtained from TA Instruments, New Castle, Del., under the trade designation "ARES G2 RHEOMETER"). The rheometer had 25 mm diameter parallel top and bottom plates. The top plate of the rheometer was brought down onto the sample of pre-adhesive composition until the parallel plates were separated by 1 mm. A temperature sweep test method was used where shear moduli, viscosity, and tan(δ) were estimated while sample was subjected to oscillatory shear (strain amplitude=1%, frequency=1 Hz) and at the same time the sample temperature was continuously increased from −65° C. to 100° C. at a rate of 5° C./min. Storage modulus (G') was reported in Pa. Viscosity (η) of the pre-adhesive composition was reported in Pascal-seconds (Pa's). Tan (δ) was calculated as the ratio of G"/G' (loss modulus/storage modulus). The temperature where the tan(δ) curve had a local peak was reported as the glass transition temperature ("$T_g$").

Percent Gel

Percent gel (gel content) was determined in generally similar manner as described in ASTM D3616-95 (as specified in 2009), with the following modifications. A test specimen measuring 63/64 inch (2.50 cm) in diameter was die-cut from a tape coated with crosslinked pressure-sensitive adhesive. The specimen was placed in a mesh basket measuring 1.5 inch (~3.8 cm) by 1.5 inch (~3.8 cm). The basket with the specimen was weighed to the nearest 0.1 mg and placed in a capped jar containing sufficient amount of EtOAc to cover the sample. After 24 hours the basket (containing the specimen) was removed, drained and placed in an oven at 120° C. for 30 minutes. The percent gel was determined by ratioing the weight of the remaining unextracted portion of the adhesive sample to the weight of the adhesive sample before extraction. (To correct for the weight of the tape backing, a disc of the uncoated backing material of the same size as the specimen was die-cut and weighed.) The formula used for percent gel determination was as shown immediately below:

$$\text{Percent Gel (wt. \%)} = \frac{100 \times (\text{unextracted sample wt. after extraction} - \text{backing wt.})}{(\text{original sample wt.} - \text{backing wt.})}$$

Peel Adhesion Test

Peel adhesion strength was measured at a 180° angle using an IMASS SP-200 SLIP/PEEL TESTER (available from IMASS, Inc., Accord, Mass.) at a peel rate of 12 inches/minute (305 mm/minute). Stainless steel test panels were prepared by wiping the substrate panels with a laboratory wipe wetted with 2-propanol using hand pressure to wipe the panel 8 to 10 times. This wiping procedure was repeated two more times with clean laboratory wipes wetted with 2-propanol. The cleaned test panels were allowed to air dry for at least 30 minutes.

Adhesive tape samples were cut into strips measuring ½ inch (~1.27 cm) by 8 inches (~20 cm), and the strips were rolled down onto the cleaned panel with a 2.0 kg rubber roller using 2 passes. The prepared samples were stored at 23° C. and 50% relative humidity for approximately 1 hour before testing. Peel strengths were reported as average values of 3 to 5 repeated experiments.

Wet-Stick Test Method

An artificial skin substrate was obtained from IMS Inc. (Portland, Me.) under the trade designation VITRO-SKIN (this material, as supplied, is formulated to mimic the topography, pH, critical surface tension etc. of human skin.) An artificial sweat liquid was made to mimic the properties of human sweat. A first ingredient (artificial sebum) was a mixture of 5.5 g of olive oil, 2.5 g of oleic acid, and 2.0 g of squalene. A second ingredient was a mixture of 3.75 g of sodium chloride, 0.75 g of urea and 0.75 g of lactic acid. The second ingredient was diluted to 750 mL in water and the pH was adjusted to 6.5 by use of $NH_4OH$. 0.375 g of the first ingredient was then vigorously mixed with the 750 ml of the second ingredient to make the artificial sweat.

Wet-stick adhesion (as a proxy for e.g. the ability to stick to wet skin) was gauged using a combination of the artificial skin substrate and the artificial sweat liquid. A 5.1 cm width×15.2 cm long piece of artificial skin was cut and placed on a stainless steel sheet by the use of a double stick tape. Approximately 0.7 mL of artificial sweat was sprayed on the top surface of the artificial skin. This was repeated four times (for a total of five separate sprays). The artificial sweat was allowed to dwell on the artificial skin for approximately three minutes, after which the artificial skin was manually dabbed dry with a lab tissue (obtained under the trade designation KIM-WIPE). The artificial sweat was again sprayed five times on the vitro skin (the artificial skin was not dabbed after this final application of artificial sweat).

Articles for wet skin adhesion testing were produced in the form of medical electrodes of the general shape and size exemplified by the product available from 3M Company under the trade designation RED DOT 2560. Each electrode measured approximately 3.5 cm by 4.0 cm, with rounded corners, and comprised a foam backing with a perimeter area upon which the PSA to be evaluated had been deposited. The perimeter area/PSA extended inward approximately 0.8 cm from each edge of the backing to form an annular border. A conductive gel was provided in the center of the electrode; the conductive gel occupied an area of approximately 2 cm by 1.8 cm (in a slightly oval shape) with the outer edges of the conductive gel being separated from the inner edges of the PSA by an annular gap. Each foam backing included a metal connector of the general type used with 3M RED DOT 2560 electrodes, a first major face of the metal connector being in contact with the conductive gel and with a stud protruding from the opposite side of the metal connector.

The sample electrode to be tested was placed on the wetted artificial skin with the PSA and conductive gel facing down and with the stud of the metal connector facing up. The electrode was pressed down against the artificial skin for two seconds using two fingers with moderate pressure. A standard EKG lead was connected to the protruding stud of the electrode. A materials testing apparatus obtained from Zwick/Roell under the trade designation Z2.5 was used to pull the EKG lead so as to apply a shear force (at essentially a zero-degree angle) to the electrode at a speed of 30.5 cm per minute. The peak in force during the pulling of the electrode (as reported in grams by the materials testing apparatus) was recorded as the Pull Force. At least three sample electrodes of any given type were tested and the average Peak Pull Force for the samples was obtained.

Preparation of Pre-Adhesive Compositions (First, Synthesis Reaction) by Photo-Initiation Preparation of Pre-Adhesive Composition PRE-1

In a transparent untinted glass jar, 75 g of IOA, 0.38 g of IRG651, 0.37 g of IOTG and 75 g of EtOAc were combined and mixed to form a homogeneous solution. Nitrogen gas was bubbled through the solution for 10 min. through a plastic tube dipped inside the solution. The glass jar was tightly capped. This sealed jar was then placed on a roller and rotated slowly for 40 min. while being exposed to UV lamps (Sylvania 35 Blacklight, Osram Sylvania Inc, Danvers, Mass.) facing down on the roller. After this period of UV exposure, the jars were opened, terminating the polymerization. The resulting pre-adhesive composition PRE-1 was dried by setting the jar containing the polymer solution inside a vacuum oven set at 100° C., until constant weight was observed. The dried pre-adhesive composition was a viscous but flowable liquid, transparent in color.

Preparation of Pre-Adhesive Compositions PRE-2 to PRE-4

Pre-adhesive compositions PRE-2 to PRE-4 were prepared using the same method as described above for PRE-1, except that the amounts of IOA, IRG651, IOTG, and EtOAc were as listed in Table 2.

TABLE 2

| Sample | IOA | | IRG651 | | IOTG | | EtOAc | |
|---|---|---|---|---|---|---|---|---|
| | parts | g | parts | g | parts | g | parts | g |
| PRE-1 | 100 | 75 | 0.5 | 0.38 | 0.49 | 0.37 | 100 | 75 |
| PRE-2 | 100 | 75 | 0.25 | 0.19 | 0.24 | 0.18 | 100 | 75 |
| PRE-3 | 100 | 75 | 0.17 | 0.13 | 0.16 | 0.12 | 100 | 75 |
| PRE-4 | 100 | 75 | 0.14 | 0.10 | 0.1 | 0.08 | 100 | 75 |

Figure 2:
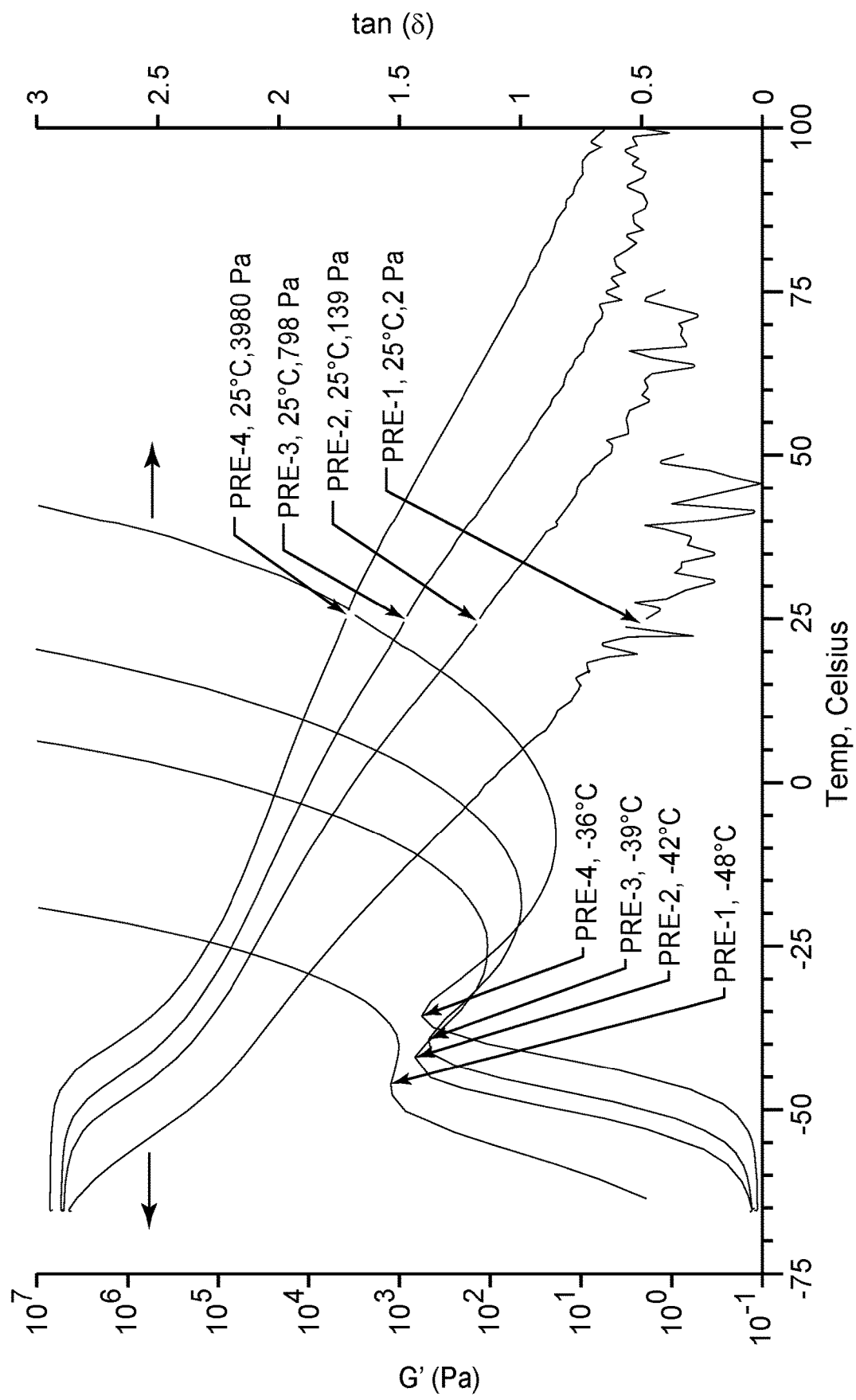
FIG. 2 presents dynamic-mechanical (DMA) data as obtained for various exemplary pre-adhesive compositions disclosed herein.

Properties for pre-adhesive compositions PRE-1 to PRE-4 were measured according to the test methods described above. DMA test data are shown in FIG. 2; test results are summarized in Table 3.

TABLE 3

| Sample | $M_n$ | $M_w$ | DP | $T_g$, ° C. | G' @25° C., Pa | η @25° C., Pa · s |
|---|---|---|---|---|---|---|
| PRE-1 | 24,400 | 52,700 | 130 | −48 | 2 | 26 |
| PRE-2 | 27,700 | 84,300 | 151 | −42 | 139 | 200 |
| PRE-3 | 34,400 | 116,000 | 187 | −39 | 798 | 474 |
| PRE-4 | 55,300 | 158,000 | 300 | −36 | 3980 | 1220 |

Preparation of Pre-Adhesive Compositions Comprising Plasticizer

Figure 3:
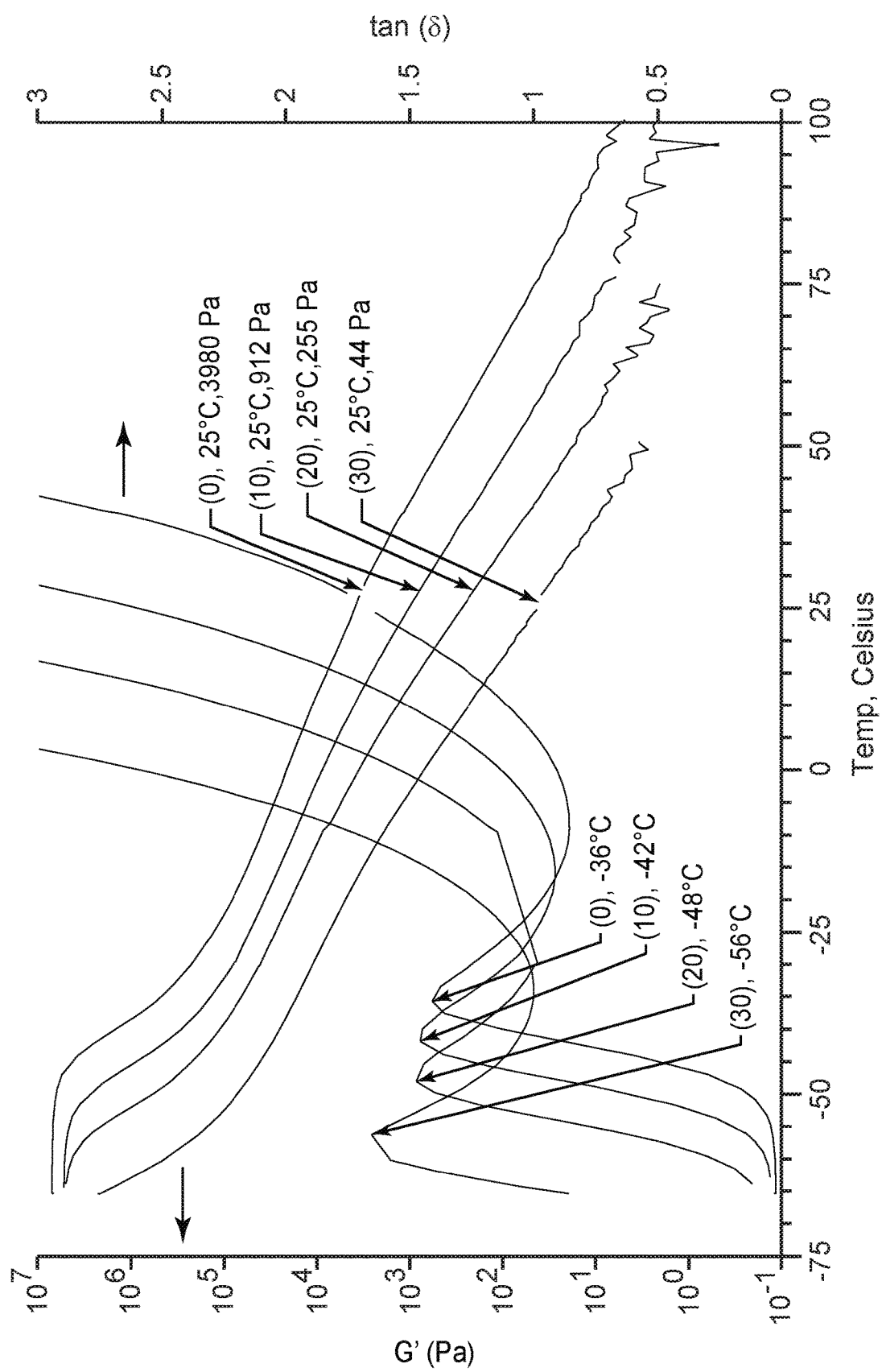
FIG. 3 presents DMA data as obtained for various additional exemplary pre-adhesive compositions disclosed herein.

Pre-adhesive composition PRE-4 was dissolved in EtOAc to 50 wt. % solids by combining PRE-4 and the requisite amount of solvent in a jar and rotating the jar for 12 hours at room temperature (ca. 22° C.) to form a homogeneous solution of PRE-4. Caprylic triglyceride (CTG) plasticizer was added dropwise to separate samples of the homogeneous solution of PRE-4, according to the ratios listed in Table 4. EtOAc solvent was then removed under reduced pressure, with heating to 100° C., until constant weight was observed. Properties for pre-adhesive compositions PRE-4 (0), (10), (20), and (30), were measured according to the test methods described above. (In these and all subsequent Samples, numbers in parentheses (xx) indicate the parts of plasticizer per parts of pre-adhesive composition.) DMA test data are shown in FIG. 3; the test results are summarized in Table 4.

TABLE 4

| Sample | PRE-4, parts | CTG, parts | $T_g$, °C. | G' @25° C., Pa | η @25° C., Pa · s |
|---|---|---|---|---|---|
| PRE-4 (0) | 100 | 0 | −36 | 3980 | 1220 |
| PRE-4 (10) | 90 | 10 | −42 | 912 | 442 |
| PRE-4 (20) | 80 | 20 | −48 | 255 | 207 |
| PRE-4 (30) | 70 | 30 | −56 | 44 | 65 |

Preparation of Pressure-Sensitive Adhesives (Crosslinking Reaction) by Ebeaming

Working Example WE-1A

A substrate (backing) was obtained (from DuPont, Wilmington, Del. under the trade designation SONTARA) that was a spunlaced nonwoven web. Pre-adhesive composition PRE-3 was heated to 70° C. for 20 minutes, and then was knife coated by hand as a 4 mil (~100 micrometers) layer on the substrate. The substrate had a polymer film of 0.8 mil (~20 micrometers) thickness on one major surface thereof; the pre-adhesive composition was coated on the same side as the polymer film. The layer of coated PRE-3 was subsequently exposed to electron beam irradiation (using an apparatus available under the trade designation CB-300 from Energy Sciences Inc., Wilmington, Mass.), operated at a setting of 230 Kilovolts (kV), to a dose of 16 Megarad (Mrad). This served to crosslink the macromolecules of the pre-adhesive composition thus transforming the pre-adhesive composition into a pressure-sensitive adhesive, thereby providing a pressure-sensitive adhesive tape comprising the nonwoven substrate with a pressure-sensitive adhesive ("PSA") layer disposed on a major surface thereof.

A test specimen of the Working Example WE-1A pressure-sensitive adhesive tape was tested in the above-described Percent Gel Test, with a resulting gel content of 62.6 wt. %. The Working Example WE-1A pressure-sensitive adhesive tape was tested in the above-described Peel Adhesion Test, with a result of 269 g/inch (106 g/cm).

Working Examples WE-1B-WE-1D, WE-2, and Comparative Examples

Additional samples of pre-adhesive composition PRE-3 were coated and treated with electron beam irradiation as described in Working Example WE-1A, except that the electron beam irradiation dosages were as summarized in Table 5. Samples of pre-adhesive composition PRE-2 were likewise coated and irradiated at various ebeam dosages, as listed in Table 5. Samples of pre-adhesive composition PRE-1 were also coated and irradiated at various ebeam dosages. However, for samples using pre-adhesive composition PRE-1, the ebeam irradiation did not appear to produce an adequately networked product (judging e.g. by the amount of residue left behind when the crosslinked polymer product was bonded and then debonded from a test surface). It thus appeared that the molecular weight of the PRE-1 pre-adhesive composition (approximately 24,400) was too low to produce an acceptable pressure-sensitive adhesive when crosslinked. Accordingly, samples made from pre-adhesive composition PRE-1 are labeled Comparative Examples herein.

180° Peel Adhesion test data are listed in Table 5 for the Working Example samples made from pre-adhesive compositions PRE-3 and PRE-2.

TABLE 5

| PSA Sample | Pre-adhesive composition | E-beam, Mrad | Peel Adhesion, g/inch (g/cm) |
|---|---|---|---|
| WE-1A | PRE-3 | 16 | 269 (106) |
| WE-1B | PRE-3 | 14 | 352 (139) |
| WE-1C | PRE-3 | 12 | 302 (119) |
| WE-1D | PRE-3 | 10 | 249 (98) |
| WE-2A | PRE-2 | 26 | 442 (174) |
| WE-2B | PRE-2 | 24 | 330 (130) |
| WE-2C | PRE-2 | 22 | 380 (150) |
| WE-2D | PRE-2 | 20 | 344 (135) |
| CE*-1A | PRE-1 | 36 | ND** |
| CE-1B | PRE-1 | 32 | ND |
| CE-1C | PRE-1 | 28 | ND |

*"CE" = Comparative Example;
**"ND" = Not Determined

In addition to Peel Adhesion tests from a test substrate (stainless steel), PSAs were also subjected to qualitative skin adhesion testing. Many such PSA samples exhibited good ability to bond to skin, and yet were able to be removed therefrom with a gentle feel (i.e., with a minimum of perceived discomfort reported by human volunteers). In particular, Working Example WE-1A exhibited excellent properties of this general nature, and was also able to be rebonded to skin several times after being removed therefrom.

Working Example PSAs Comprising Plasticizer

Samples of pre-adhesive composition PRE-4 (10), PRE-4 (20), and PRE-4 (30), comprising various amounts of plasticizer as noted above, were coated onto a backing and treated with electron beam irradiation as described in Working Example WE-1A. The ebeam dosages used varied from 16 to 28 Mrad. In qualitative testing, the resulting PSA's typically displayed a gentle feel in removal from human skin, with slightly more residue being noted at the highest levels of plasticizer.

Pre-Adhesive Compositions and Working Example PSAs Using Other Monomers

Preparation of Pre-Adhesive Composition PRE-5 and PRE-5 (10)

A composition PRE-5 was made by the same method used for PRE-3, except that the monomer used was EHA (instead of IOA). Plasticizer (CTG) was then added to form a pre-adhesive composition PRE-5 (10) using the same method as used for PRE-4 (10).

Preparation of Pre-Adhesive Composition PRE-6 and PRE-6 (10)

A composition PRE-6 was made by the same method used for PRE-3, except that the monomer used was DDA (instead of IOA), and that the ratio of reactants were as shown in Table 6. Plasticizer (CTG) was then added to form a pre-adhesive composition PRE-6 (10) using the same method as used for PRE-4 (10).

TABLE 6

| Sample | DDA parts | g | IRG651 parts | g | IOTG parts | g | EtOAc parts | g |
|---|---|---|---|---|---|---|---|---|
| PRE-6 | 100 | 75 | 0.15 | 0.1125 | 0.1 | 0.075 | 100 | 75 |

TABLE 6-continued

| | DDA | | IRG651 | | IOTG | | EtOAc | |
|---|---|---|---|---|---|---|---|---|
| Sample | parts | g | parts | g | parts | g | parts | g |

Working Example WE-3

A PSA Sample WE-3 was made in the same method as WE-1A, except that pre-adhesive composition PRE-5 (10) was used, the knife coating gap during coating was set at 7 mils, and the ebeam setting was 200 KV. The resulting Working Example WE-3 pressure-sensitive adhesive tape was tested in the above-described Peel Adhesion Test, with a result of 276 g/inch (109 g/cm).

Working Example WE-4

A PSA Sample WE-4 was made in the same method as WE-1A, except that pre-adhesive PRE-6 (10) was used, the knife coating gap during coating was set at 7 mils, and the ebeam setting was 240 KV. The resulting Working Example WE-4 pressure-sensitive adhesive tape was tested in the above-described Peel Adhesion Test, with a result of 194 g/inch (77 g/cm).

TABLE 7

| PSA Sample | Pre-adhesive composition | E-beam, Mrad | Peel Adhesion, g/inch (g/cm) |
|---|---|---|---|
| WE-3 | PRE-5 (10) | 16 | 276 (109) |
| WE-4 | PRE-6 (10) | 16 | 194 (77) |

Pre-Adhesive Compositions and Working Example PSAs Including Hydrocolloids

Preparation of Pre-Adhesive Composition Series PRE-7

A composition PRE-7 was made by the same method, and of approximately the same composition, as PRE-3. 10 parts plasticizer (CTG) was then added to composition PRE-7 by the same method as used to make composition PRE-4 (10). Composition PRE-7 (10) was mixed with hydrocolloid (CMC) at various proportions, to form various hydrocolloid-containing pre-adhesive compositions as shown in Table 8 below. The pre-adhesive compositions were rolled over rollers for 6 hours. (In all samples below, the parts of hydrocolloid in the pre-adhesive composition are shown in square brackets [yy]; the parts of plasticizer are shown in parentheses.)

TABLE 8

| Sample | PRE-7 (10), parts | CMC, parts |
|---|---|---|
| PRE-7 (10) [0] | 100 | 0 |
| PRE-7 (10) [5] | 100 | 5 |
| PRE-7 (10) [10] | 100 | 10 |
| PRE-7 (10) [15] | 100 | 15 |
| PRE-7 (10) [20] | 100 | 20 |

Working Examples WE-5A to WE-5E

PSA Samples WE-5A to WE-5E were made by the same method as used for Sample WE-1A, except that the knife coating gap during coating was set at 7 mils (instead of 4 mils). The Working Examples adhesive tapes were tested in the above-described Peel Adhesion Test, with results shown as below:

TABLE 9

| PSA Sample | Pre-adhesive composition | E-beam, Mrad | Peel Adhesion, g/inch (g/cm) |
|---|---|---|---|
| WE-5A | PRE-7 (10) [0] | 16 | 282 (111) |
| WE-5B | PRE-7 (10) [5] | 16 | 299 (118) |
| WE-5C | PRE-7 (10) [10] | 16 | 293 (115) |
| WE-5D | PRE-7 (10) [15] | 16 | 294 (116) |
| WE-5E | PRE-7 (10) [20] | 16 | 248 (98) |

Preparation of Pre-Adhesive Compositions (First, Synthesis Reaction) by Thermal Initiation Preparation of Pre-Adhesive Composition PRE-101

In a tinted glass jar, 100 parts (grams) of IOA monomer, 0.4 g of AeBP, 0.14 g of VA67, 0.14 g of IOTG, and 100 g of EtOAc were combined to form a reaction mixture. The mixture was well mixed using a shaker and formed a homogenous solution. Nitrogen gas was bubbled through the solution for 10 minutes. The cap of the jar was tightened and the jar was put in a launderomater containing water maintained at a setpoint of 60° C. and the reaction was allowed to proceed. After approximately 24 hours of reaction time, the glass jar was removed from the launderomater and opened to allow air/oxygen to enter the jar, thereby terminating the reaction.

Preparation of Pre-Adhesive Compositions PRE-102 to PRE-107

Pre-adhesive compositions PRE-102 to PRE-107 were prepared using the same method as described above for PRE-101, except that the parts of IOA, AeBP, VA67, IOTG, and EtOAc were as listed in Table 10. (Samples 106i-106v differed only in the amount of AeBP.)

TABLE 10

| Sample | IOA | AeBP | VA67 | IOTG | EtOAc |
|---|---|---|---|---|---|
| PRE-101 | 100 | 0.4 | 0.14 | 0.14 | 100 |
| PRE-102 | 100 | 0.2 | 0.2 | 0.15 | 100 |
| PRE-103 | 100 | 0.15 | 0.2 | 0.15 | 100 |
| PRE-104 | 100 | 0.1 | 0.2 | 0.15 | 100 |
| PRE-105 | 100 | 0.2 | 0.2 | 0.23 | 100 |
| PRE-106i | 100 | 0.2 | 0.2 | 0.35 | 100 |
| PRE-106ii | 100 | 0.4 | 0.2 | 0.35 | 100 |
| PRE-106iii | 100 | 0.6 | 0.2 | 0.35 | 100 |
| PRE-106iv | 100 | 0.8 | 0.2 | 0.35 | 100 |
| PRE-106v | 100 | 1 | 0.2 | 0.35 | 100 |
| PRE-107 | 100 | 0.2 | 0.2 | 0.55 | 100 |

Molecular weights and degrees of polymerization for pre-adhesive compositions PRE-101 to PRE-107 were measured according to the test methods described above and are summarized in Table 11.

TABLE 11

| Sample | $M_n$ | $M_w$ | DP |
|---|---|---|---|
| PRE-101 | 71,300 | 242,000 | 388 |
| PRE-102 | 57,900 | 174,000 | 315 |
| PRE-103 | 56,600 | 164,000 | 308 |
| PRE-104 | 55,100 | 168,000 | 299 |
| PRE-105 | 57,900 | 163,000 | 315 |
| PRE-106i | 43,100 | 106,000 | 234 |
| PRE-106ii | 34,500 | 86,000 | 188 |
| PRE-106iii | 31,700 | 89,000 | 172 |
| PRE-106iv | 33,400 | 84,000 | 182 |

TABLE 11-continued

| Sample | $M_n$ | $M_w$ | DP |
|---|---|---|---|
| PRE-106v | 32,400 | 82,000 | 176 |
| PRE-107 | 32,100 | 76,000 | 175 |

Preparation of Pressure-Sensitive Adhesives (Crosslinking Reaction) by Photo-Crosslinking Working Example WE-101

90 parts of pre-adhesive composition PRE-106iii were mixed with 10 parts of CTG plasticizer until a homogenous solution was obtained. The solution was then coated manually, with a laboratory knife coater with a coating gap of approximately 10 mils, onto a tape backing of the type found in the product available in 2014 from 3M Company, St. Paul Minn. under the trade designation KIND REMOVAL SILICONE TAPE. The coated tape backing was then placed (coating side up) in an oven for 70° C. for twenty minutes to remove the solvent. After this, the coated tape backing was exposed to high intensity UV radiation (UV-B, "D" bulb) for a total dose of approximately 270 mJ/cm². The resulting pressure-sensitive adhesive tape was found to exhibit a Peel Adhesion of approximately 220 grams/inch.

Preparation of a Solventless Pre-Adhesive Composition

A reaction mixture was prepared with 100 parts IOA, 0.3 parts AeBP, 0.16 parts IOTG, and various thermal initiators and antioxidants. The reaction mixture was reacted in a first reaction step, after which various additional thermal initiators and antioxidants were added and a second reaction step was performed. (The combinations of thermal initiators and antioxidants and two-step procedure that was used, followed the general teachings outlined in the Examples of U.S. Pat. No. 7,968,661 to Ellis.) The AeBP and certain thermal initiators were provided in EtOAc to ensure that they were dissolved, thus a very small amount of solvent was present in this nominally solventless reaction mixture. The thus-produced pre-adhesive composition had a molecular weight ($M_n$) of approximately 75,400 grams per mole.

The pre-adhesive composition was dried in a vacuum oven at 100° C. for two hours, after which it was dissolved in EtOAc at approximately 50% solids. (The composition was dissolved in solvent for ease of hand-coating without needing to heat the composition for coating.) 90 parts of this pre-adhesive composition was mixed with 10 parts of CTG plasticizer until a homogenous solution was obtained. The solution was then coated manually, with a laboratory knife coater with a coating gap of approximately 3 mils, onto a tape backing. The coated tape backing was then placed (coating side up) in an oven for 70° C. for twenty minutes to remove the solvent. After this, the coated tape backing was exposed to high intensity UV radiation (UV-B D bulb) for a total dose of approximately 180 mJ/cm². The resulting pressure-sensitive adhesive tape was found to exhibit a Peel Adhesion of approximately 163 grams/inch. The PSA was also subjected to qualitative skin adhesion testing, and was found to evoke a feeling that was gentle on skin during removal.

Wet-Stick Adhesion Testing

A pre-adhesive composition was made using a solventless procedure generally similar to that described above. The pre-adhesive composition comprised essentially linear poly (ethylhexyl acrylate) macromolecules with a measured number-average molecular weight of approximately 40000 grams/mole. Caprylic triglyceride (CTG) plasticizer was mixed into the pre-adhesive composition to obtain a weight ratio of 95/5 pEHA/CTG. The pre-adhesive composition was coated onto a polyethylene closed-cell foam substrate of the general type used as a backing in the product available from 3M Company, St. Paul Minn., under the trade designation RED DOT ELECTRODE 2560. The thickness of the foam substrate was estimated to be approximately 1.6 mm; the pre-adhesive composition was coated onto a surface of the foam substrate to a final thickness of approximately 75 microns. The coated pre-adhesive composition was then irradiated with electron beam to a dose of 12 Mrad, at 220 kV, to crosslink the macromolecules with each other so as to convert the pre-adhesive composition into a PSA. Two different Working Example sample sets were made, one (labeled "E-1" in resulting data set) with the foam substrate surface (upon which the pre-adhesive composition was deposited) having been primed, the other (labeled "E-2" in the resulting data set) with the foam unprimed.

Figure 4:
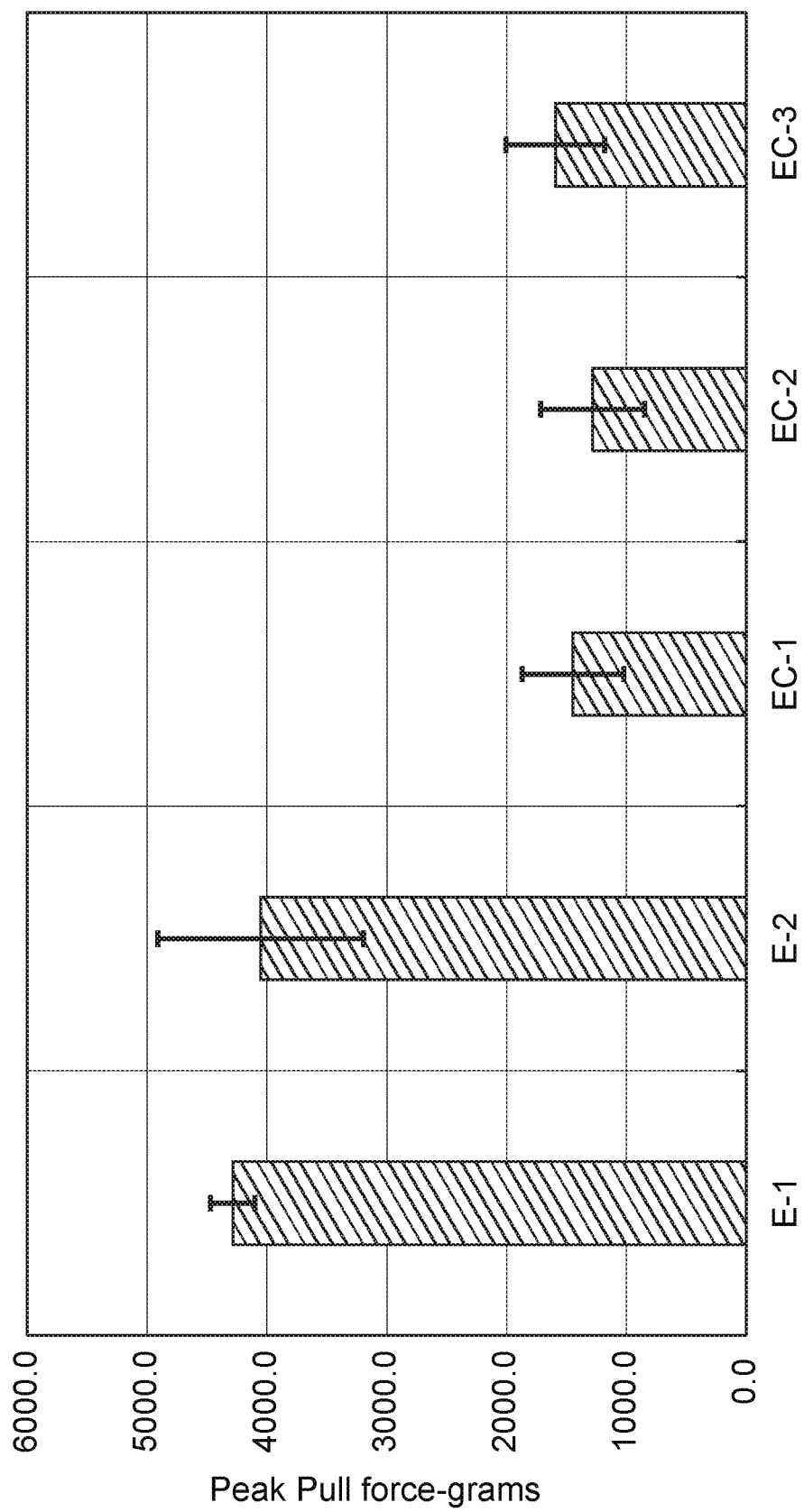
FIG. 4 presents Wet-Stick Adhesion Test data for various Working and Comparative Examples.

The foam substrate samples with ebeam-cured PSA thereon were then converted to electrodes as described in the Wet Stick Test Method, and then tested according to the Method. The size of the Working Example electrodes was approximately 3.5×4.0 cm as noted in the Wet Stick Test Method. Three commercially available electrodes were tested as comparative examples EC-1, EC-2, and EC-3. The electrodes of comparative example EC-2 were of the same approximate size and shape as the Working Example electrodes. The electrodes of comparative example EC-1 were larger (approximately 5.0×5.5 cm) than the Working Example electrodes, and were of similar shape (rectangular with rounded corners). The electrodes of comparative example EC-3 were somewhat teardrop shaped with a long dimension of approximately 4.9 cm and a short dimension of approximately 4.5 cm. The test results are presented in FIG. 4.

The foregoing Examples have been provided for clarity of understanding only, and no unnecessary limitations are to be understood therefrom. The tests and test results described in the Examples are intended to be illustrative rather than predictive. All quantitative values in the Examples are understood to be approximate in view of the commonly known tolerances involved. It will be apparent that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is a conflict or discrepancy between this specification as written and the disclosure in any document incorporated by reference herein, this specification as written will control.

What is claimed is:

1. A wet-stick pressure-sensitive adhesive article, comprising:
a substrate comprising a wet-stick pressure-sensitive adhesive on a major surface of the substrate,
the wet-stick pressure-sensitive adhesive being a crosslinking reaction product of a pre-adhesive composition,
the pre-adhesive composition comprising poly(meth)acrylate macromolecules characterized by a number-average molecular weight of about 25000 to about 200000,
wherein the poly(meth)acrylate macromolecules are present in an amount of at least 90 wt % of the pre-adhesive composition, and
wherein the pre-adhesive composition exhibits a glass transition temperature (Tg) of less than minus 20° C. and exhibits a storage modulus of about 4 Pa to about 10000 Pa at 25° C.

2. The adhesive article of claim 1, wherein the poly(meth)acrylate macromolecules are characterized by a number-average molecular weight of from about 25000 to about 100000.

3. The adhesive article of claim 1, wherein the poly(meth)acrylate macromolecules are characterized by a number-average molecular weight of from about 25000 to about 40000.

4. The adhesive article of claim 1, wherein the pre-adhesive composition exhibits a storage modulus of about 100 Pa to about 1000 Pa at 25° C.

5. The adhesive article of claim 1, wherein the pre-adhesive composition exhibits a viscosity of about 10 Pa·s to about 800 Pa·s at 25° C.

6. The adhesive article of claim 1, wherein the poly(meth)acrylate macromolecules are present in an amount of at least 95 wt. % of the pre-adhesive composition.

7. The adhesive article of claim 1, wherein the (meth)acrylate monomers consist essentially of nonpolar (meth)acrylate monomers with a Tg of less than 0° C.

8. The adhesive article of claim 1, wherein the (meth)acrylate monomers consist essentially of alkyl (meth)acrylate monomers.

9. The adhesive article of claim 1, wherein the poly(meth)acrylate macromolecules are substantially linear macromolecules.

10. The adhesive article of claim 1, wherein the wet-stick pressure-sensitive adhesive exhibits a Peak Pull Force of at least 3000 g when tested according to the Wet-Stick Test Method.

11. The adhesive article of claim 1, the pre-adhesive composition further comprising about 2 wt. % to about 10 wt. % of a plasticizer, based on the total weight of the pre-adhesive composition.

12. The adhesive article of claim 1, the pre-adhesive composition further comprising a chain transfer agent.

13. The adhesive article of claim 1, wherein the wet-stick pressure-sensitive adhesive exhibits a gel content of about 40 to about 70%.

14. The adhesive article of claim 1, wherein the crosslinking reaction product is formed via e-beam.

15. The adhesive article of claim 1, the pre-adhesive composition further comprising a photo-activatable crosslinker monomer, wherein the crosslinking reaction product is formed via photo-irradiation.

16. The adhesive article of claim 1, selected from the group consisting of a medical tape, an adhesive bandage, a wound dressing, a wound closure strip, a surgical drape, and a cannula retention device.

17. The adhesive article of claim 1, selected from the group consisting of a monitoring or diagnostic electrode, a patient grounding plate, a transcutaneous electrical nerve stimulation device, a transdermal drug delivery device, and an ostomy appliance.

18. The adhesive article of claim 1, with the proviso that the adhesive article does not comprise a pressure-sensitive adhesive other than the wet-stick pressure-sensitive adhesive.

19. A method of bonding the adhesive article of claim 1 to skin, the method comprising:
contacting the wet-stick pressure-sensitive adhesive of the adhesive article to the skin.

20. The method of claim 19, with the proviso that no pressure-sensitive adhesive other than the wet-stick pressure-sensitive adhesive is used to bond the adhesive article to the skin.

* * * * *